(12) United States Patent
Sakai et al.

(10) Patent No.: US 7,197,932 B2
(45) Date of Patent: Apr. 3, 2007

(54) FAILURE DETECTING SYSTEM

(75) Inventors: Masayoshi Sakai, Kuki (JP); Toshihito Shirai, Kuki (JP); Akira Morisada, Kuki (JP)

(73) Assignee: The Nippon Signal Co, Ltd., Tokyo (JP)

( * ) Notice: Subject to any disclaimer, the term of this patent is extended or adjusted under 35 U.S.C. 154(b) by 703 days.

(21) Appl. No.: 10/129,016

(22) PCT Filed: Sep. 4, 2000

(86) PCT No.: PCT/JP00/06000

§ 371 (c)(1),
(2), (4) Date: Apr. 30, 2002

(87) PCT Pub. No.: WO02/21119

PCT Pub. Date: Mar. 14, 2002

(65) Prior Publication Data

US 2006/0010979 A1  Jan. 19, 2006

Related U.S. Application Data

(63) Continuation of application No. PCT/JP00/08549, filed on Dec. 1, 2000.

(30) Foreign Application Priority Data

Sep. 4, 2000    (WO) .................. PCT/JP00/06000
Dec. 1, 2000    (WO) .................. PCT/JP00/08549

(51) Int. Cl.
*G01N 29/04*   (2006.01)
*G01N 29/07*   (2006.01)
*G01N 29/38*   (2006.01)

(52) U.S. Cl. .................. 73/598; 73/626; 73/628; 73/636

(58) Field of Classification Search .............. None
See application file for complete search history.

(56) References Cited

U.S. PATENT DOCUMENTS 3,768,306 A * 10/1973 Stearns ................. 73/625

(Continued)

FOREIGN PATENT DOCUMENTS

EP   0 861 764 A1   2/1998

(Continued)

*Primary Examiner*—Hezron Williams
*Assistant Examiner*—John C. Hanley
(74) *Attorney, Agent, or Firm*—Lawrence E. Laubscher, Jr.

(57) ABSTRACT

The present invention relates to a failure detecting system that enables the detection of a break in a rail and the like by a simple network configuration. Detecting units (20 and 50), relay units (30A, 30B, 60A through 60C) and terminal units (40 and 70) are arranged along rails (11, 11A and 11B). Using the rails (11, 11A and 11B) as transmission media, ultrasonic waves transmitted from the detecting units (20 and 50) are transmitted to the terminal units (40 and 70) by the relay units (30A, 30B, 60A through 60C), and when the terminal units (40 and 70) receive the ultrasonic waves, the ultrasonic waves are returned from the terminal units (40 and 70), relayed by the relay units (30A, 30B, 60A through 60C), and transmitted to the detecting units (20 and 50). Thus, it is judged whether there is a break in the rails (11, 11A and 11B), based on the ultrasonic wave reception state in the detecting units (20 and 50).

19 Claims, 25 Drawing Sheets

U.S. PATENT DOCUMENTS 3,996,791 A * 12/1976 Niklas et al. ............. 73/602
4,301,684 A * 11/1981 Thompson et al. ......... 73/602
4,457,178 A * 7/1984 Turbe et al. ............. 73/636
4,487,071 A * 12/1984 Pagano et al. ............ 73/612
5,386,727 A * 2/1995 Searle .................... 73/602
5,743,495 A    4/1998 Welles, II et al.
6,055,862 A * 5/2000 Martens ................. 73/632

FOREIGN PATENT DOCUMENTS

JP   56-128542    9/1981
WO   WO 98/07610  2/1998

* cited by examiner

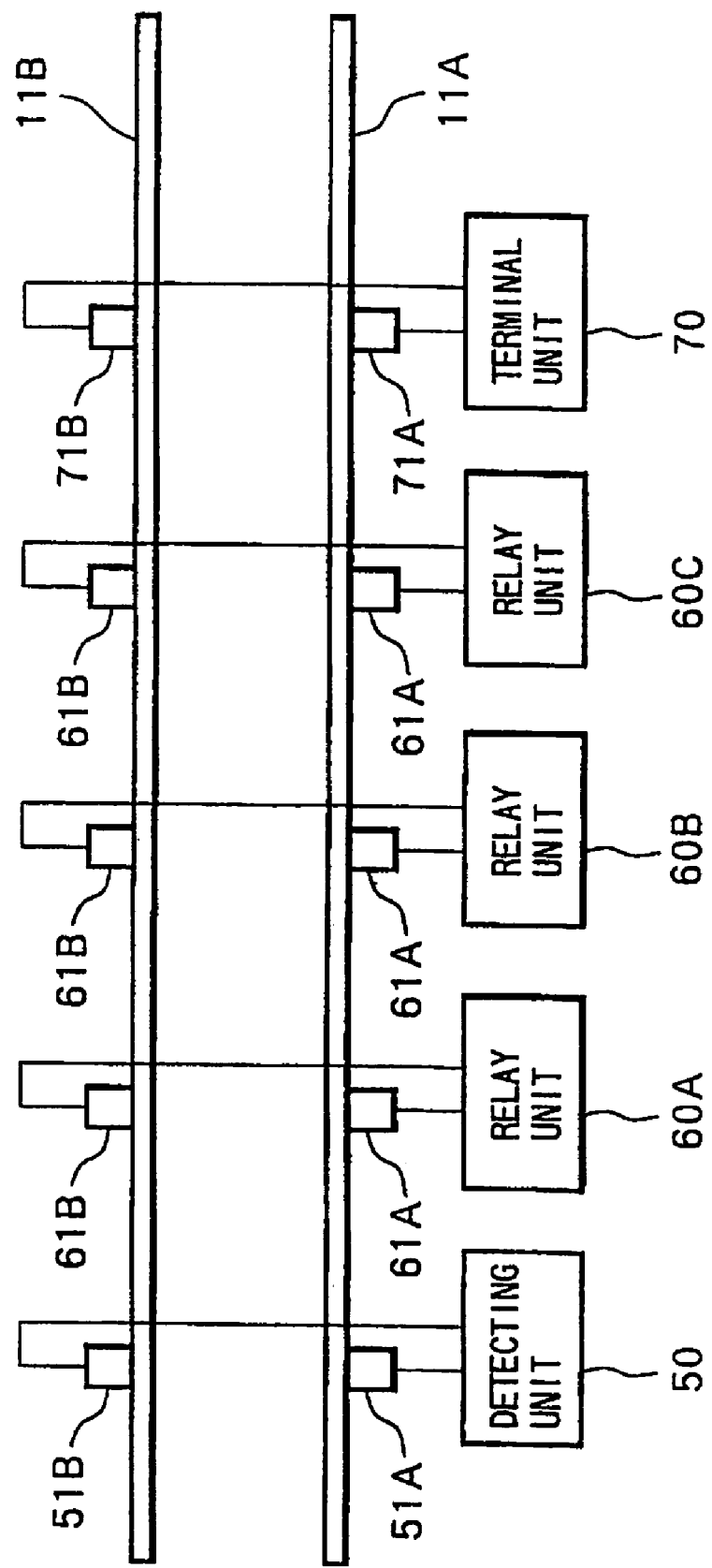

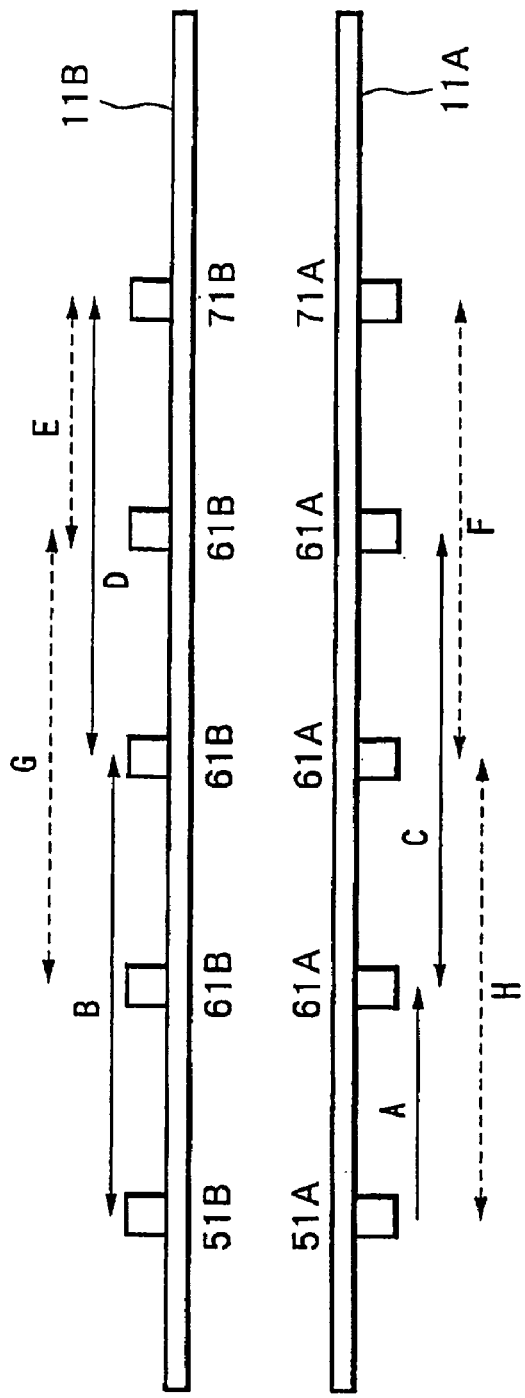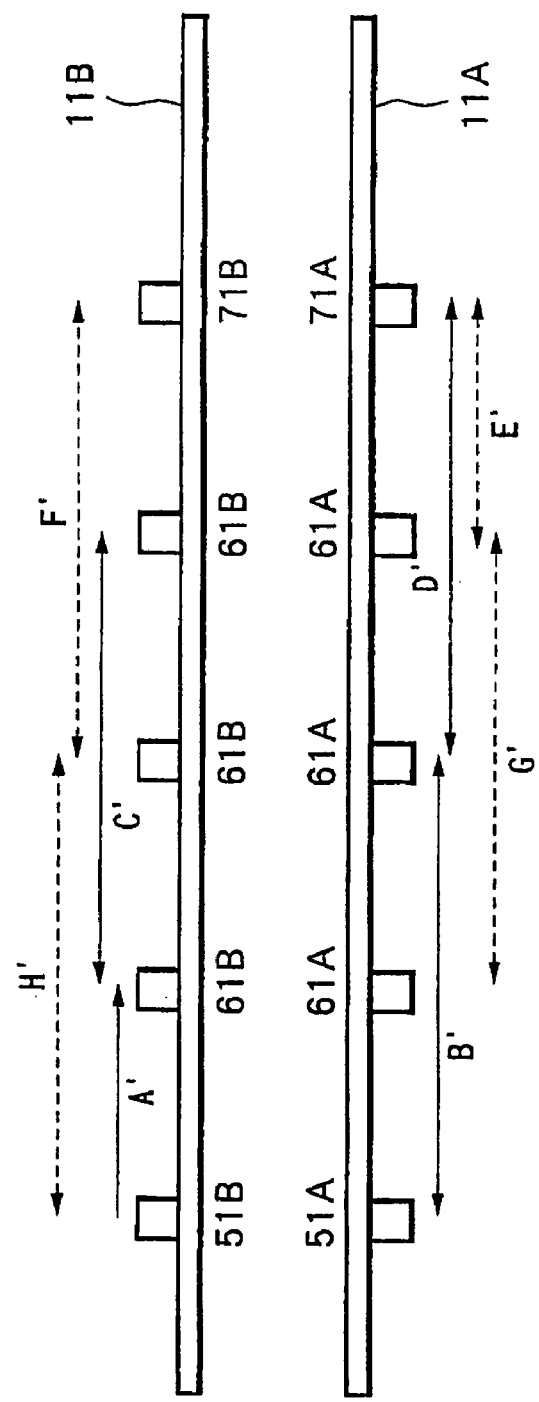

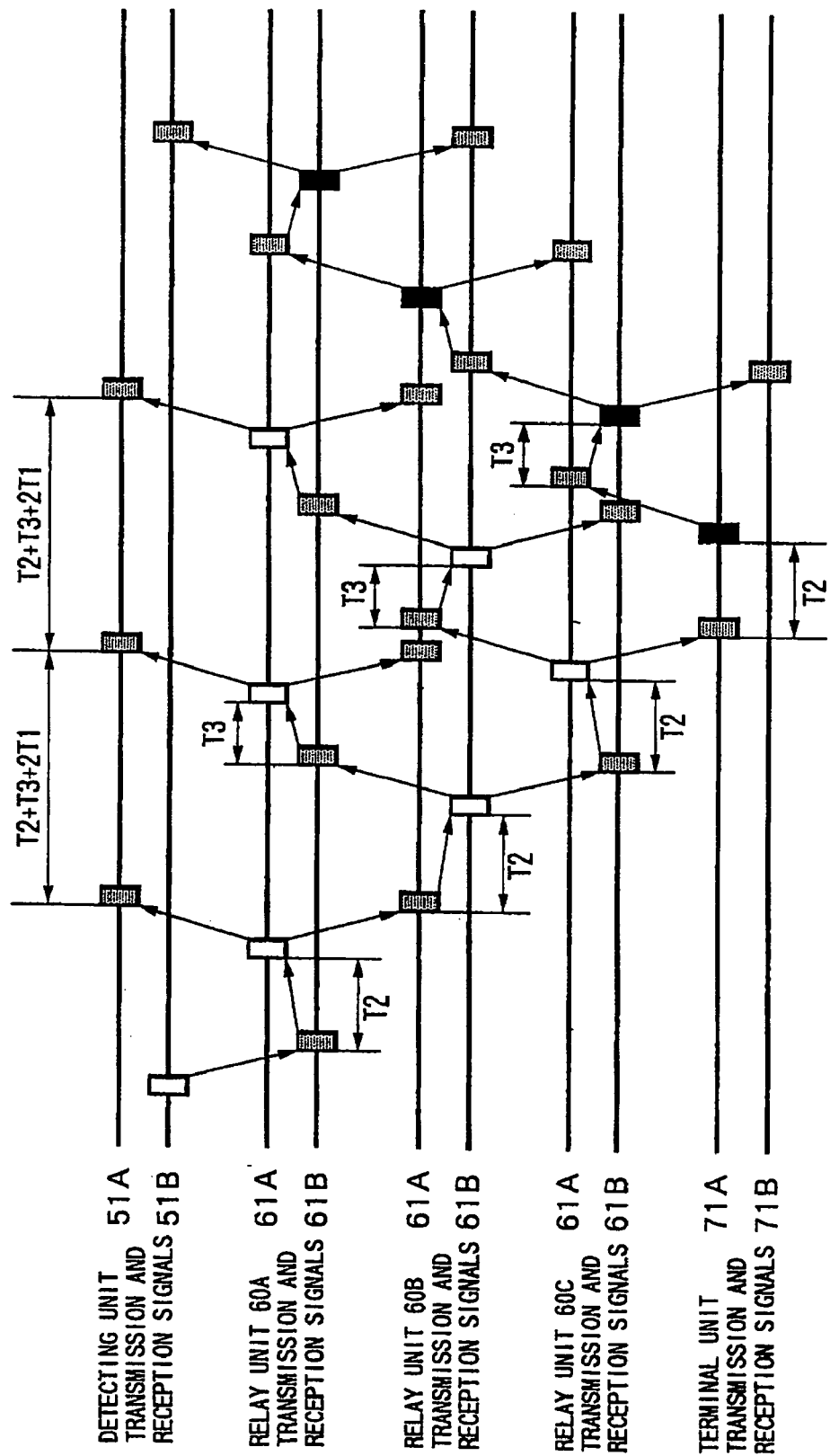

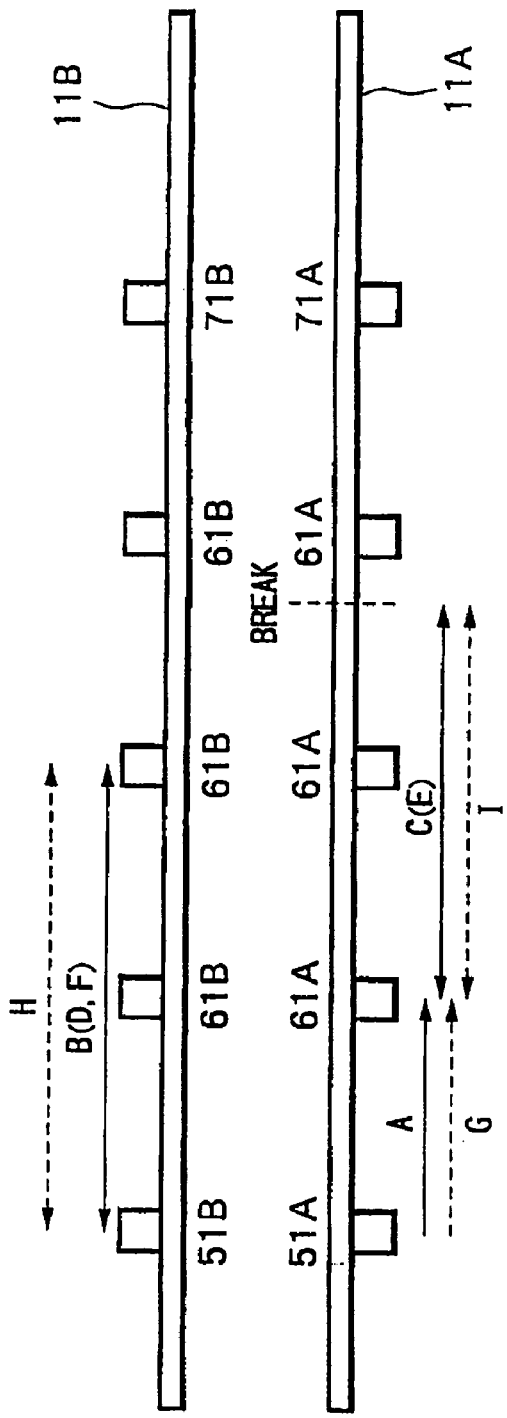
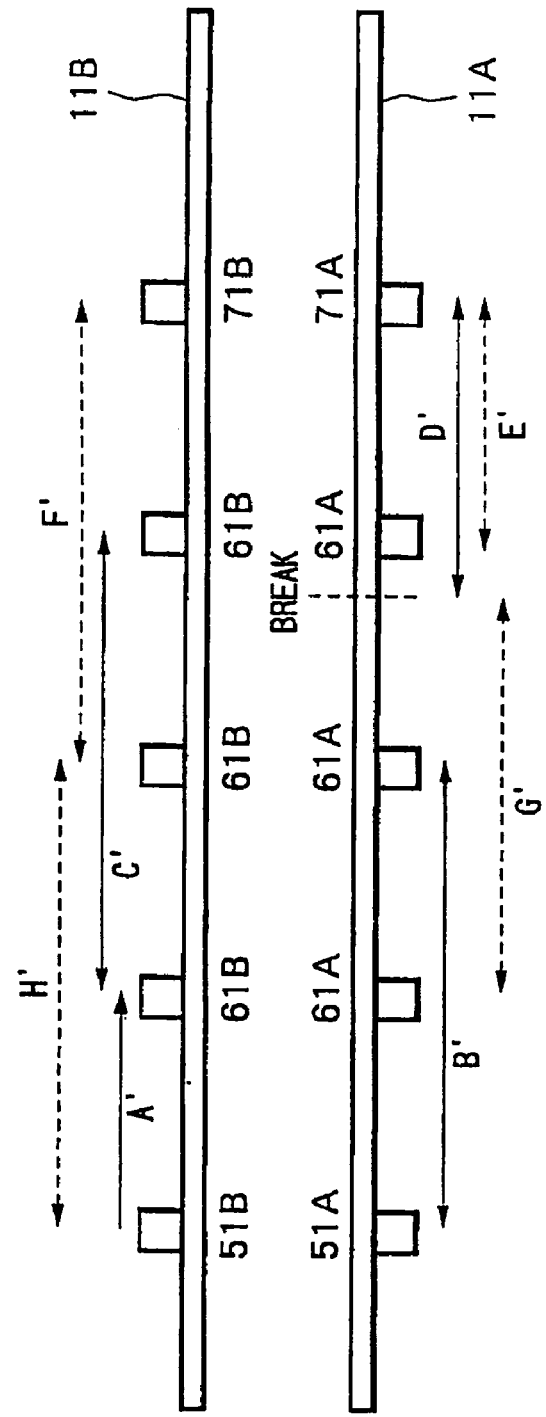

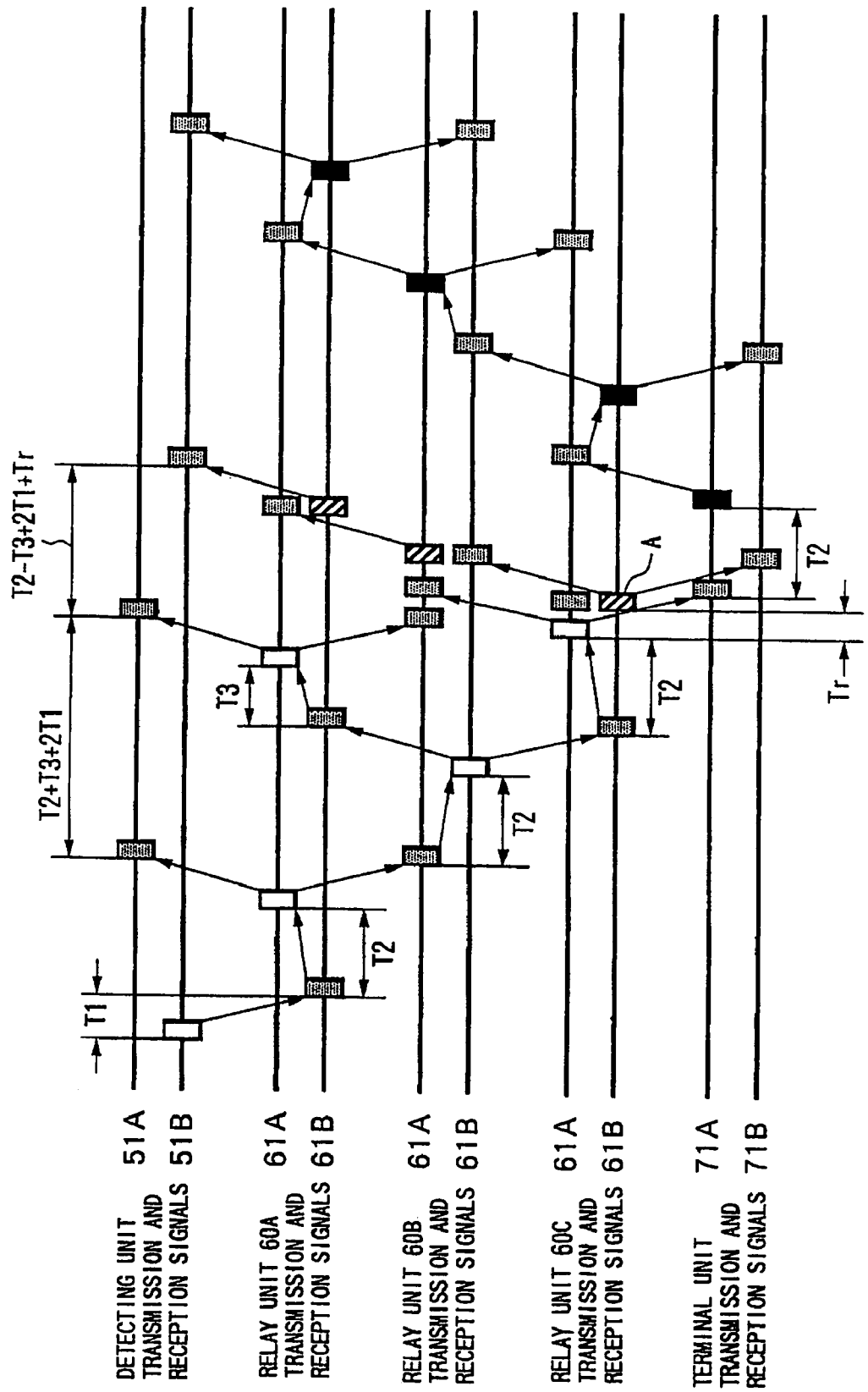

US 7,197,932 B2

FAILURE DETECTING SYSTEM

This application is a continuation of PCT/JP00/08549 filed on Dec. 1, 2000.

TECHNICAL FIELD

The present invention relates to a failure detecting system for detecting failures such as breaks and the like in rails or pipes laid over long distances by using sound wave. In particular, the present invention relates to a technique for achieving simplification of such a system.

BACKGROUND ART

For example, in the field of railway signalling, a detection of train is performed by using track circuits. However, as a secondary function, these track circuits are provided with rail failure detecting functions for detecting whether there is a break in the rails.

Incidentally, in recent years, train detecting systems using radio transmission for the purpose of facilitation of safety have been considered. In the case where a train detecting system using radio transmission is adopted, since this system does not have a function for detecting rail breaks, it is necessary to provide separately a facility for detecting rail failures such as breaks and the like. An advantage of a train detecting system using radio transmission is that signal line cabling is not required. Accordingly, it is desirable for a rail failure detecting apparatus used together with a train detecting system using radio transmission to be one that does not require the signal line cabling.

For such a rail failure detecting system, systems using ultrasonic waves are well known (refer to International Publication WO98/7610 and U.S. Pat. 5,743,495).

FIG. 1 shows an example of a conventional break detecting system for detecting rail breaks over a long distance using ultrasonic waves.

In FIG. 1, a large number of terminal devices $2_1$, $2_2$, $2_3$, . . . are installed at intervals along a rail 1. The terminal devices $2_1$, $2_2$, $2_3$, . . . are provided with ultrasonic wave transmitter-receivers $3_1$, $3_2$, $3_3$, . . . and communication units $4_1$, $4_2$, $4_3$, . . . respectively, and are connected to a central processing unit 5 via a communication line 6 so as to be able to communicate with the central processing unit 5.

In this conventional system, ultrasonic waves are transmitted from each terminal device to the next terminal device such that the terminal device $2_1$ transmits ultrasonic waves to the next terminal device $2_2$, the terminal device $2_2$ transmits ultrasonic waves to the next terminal device $2_3$, and the terminal device $2_3$ transmits ultrasonic waves to the next terminal device. Each of the terminal devices $2_1$, $2_2$, $2_3$, . . . periodically informs the central processing unit 5, through each of the communication units $4_1$, $4_2$, $4_3$, . . . , whether ultrasonic waves have been transmitted or received.

For example, if a rail break occurs between the terminal device $2_1$ and the terminal device $2_2$, an ultrasonic wave signal transmitted from the terminal device $2_1$ is not received by the terminal device $2_2$. If there is no information from the terminal device $2_2$ to the central processing unit 5 that the signal has been received, then the central processing unit 5 judges that there is a break in the rail between the terminal device 2, and the terminal device $2_2$.

Furthermore, in the case where the location of a rail break is detected by the system in FIG. 1, when each of the terminal devices $2_1$, $2_2$, $2_3$, . . . receives reflected waves, it immediately informs the central processing unit 5 that reflected waves have been received. The central processing unit 5 can calculate the location where reflection occurred, that is, the location of a break in the rail, based on the time the ultrasonic waves were transmitted and the time the reflected waves were received.

Incidentally, the transmission distance of ultrasonic waves depends on the form and installation condition of an ultrasonic transmission medium. For example, in the case of a pipe, equipments for fitting pipe increase the attenuation of ultrasonic waves. Furthermore, in the case of a rail, the attenuation of ultrasonic waves becomes large by sleeper and rail fastenings. Generally, the detection range in the case of pipe failure detection using reflection of ultrasonic waves is approximately few score meters, and the detection range in the case of rail break detection is from 1 to 2 km.

Therefore, in the case of detecting breaks in a rail or pipe installed over a long distance, in the conventional system in FIG. 1, if the number of terminal devices connected to the central processing unit via the communication line is increased, there is a problem in that control of the network comprising terminal devices, communication lines and a central processing unit becomes complicated.

A method has also been reported for performing long distance transmission by generating powerful ultrasonic waves. However, since there are possibilities of the ultrasonic wave generating apparatus becoming too big, and the ultrasonic transmission medium itself getting damaged, it is difficult to utilize such a method for detecting breaks in pipes and rails.

The present invention takes such conventional problems into consideration, and has an object of providing a failure detecting system capable of reducing the number of terminal devices connected to a communication line of a network, and also simplifying the network.

DISCLOSURE OF THE INVENTION

In order to achieve the above object, the construction of a failure detecting system of the present invention is such that a detecting unit, relay units and a terminal unit are arranged along a detection object at intervals, sound wave transmitted from the detecting unit is relayed by the relay units to be transmitted to the terminal unit using the detection object as a transmission medium, and when the terminal unit receives the transmitted sound wave, the sound wave is returned from the terminal unit, and relayed by the relay units to be transmitted to the detecting unit, so that it is judged whether or not there is a failure in the detection object, based on the sound wave reception state in the detecting unit.

According to such a construction, the sound wave reception state may be monitored in the detecting unit, and even in the case where failures such as breaks and the like in a detection object are detected over a long distance, only the detecting unit need be connected to a central processing unit or the like via a communication line. Therefore, it is possible to simplify the communication network.

Furthermore, each of the relay unit is provided with a first transmission and reception section that transmits and receives sound wave on the detecting unit side, and a second transmission and reception section that transmits and receives sound wave on the terminal unit side, wherein when the first transmission and reception section receives sound wave from the detecting unit side, the second transmission and reception section transmits the sound wave to the terminal unit side, and when the second transmission and reception section receives the sound wave from the terminal unit side, the first transmission and reception section transmits the sound wave to the detecting unit side. If the construction is such that when the relay unit receives sound wave from the detecting unit side, the first transmission and reception section returns the sound wave to the detecting unit side, then in a case where there is no failure in the detection object, since reception signals corresponding to the number of installed relay units and terminal unit are received, it is possible to monitor the operating states of the relay units and the terminal unit. Moreover, when reflected sound wave is received from a failure, since a location of failure can be specified based on the time from the reception signal immediately beforehand to the reception signal by the reflected sound wave, it is possible to suppress errors in detecting the location of failure caused by a difference in timing from receiving to transmitting in the relay unit, and hence the location of failure can be specified accurately. Furthermore, in the detecting unit, it is possible to correct a change in sound wave propagation speed caused by the installation environment and the like, based on the time from when the detecting unit transmits sound wave to when it receives the sound wave transmitted to the direction of the detecting unit by the adjacent relay unit that received the sound wave, and hence the location of failure can be specified accurately.

If the sound wave transmission levels of the relay unit and the terminal unit are set to be almost the same as the reflected sound wave level in the vicinity of where these units are arranged, then it is possible to check whether the detecting unit and the relay unit maintain the ability to receive reflected sound wave, respectively.

Furthermore, the construction may be such that the relay unit comprises at least a transmission and reception section that transmits and receives sound wave in the directions of both the detecting unit side and the terminal unit side.

In such a construction, it is becomes possible to easily install a transmission and reception section for a detection object.

In this case, the relay unit is constructed to transmit sound wave with a preset time delay after received the sound wave. If the construction is such that the time delay is different between when sound wave is received for the first time and when sound wave is received for a second or later time, it is possible to differ the transmission timing of each relay unit from each other, so that interference due to received sound wave can be avoided.

Furthermore, the construction may be such that when the relay unit receives a sound wave signal from the terminal unit, it transmits the same signal as the sound wave signal returned from the terminal unit, and after transmission, the relay of the signal is stopped.

In such a construction, it is possible to avoid unnecessary transmission of sound wave.

Moreover, the construction may be such that when the relay unit receives reflected sound wave from a failure in a detection object, it transmits a signal indicating reception of the reflected sound wave, which is different from any of a sound wave signal transmitted from the detecting unit and a sound wave signal returned from the terminal unit.

Furthermore, the construction may be such that the transmission and reception sections of each the detecting unit, the relay unit and the terminal unit are installed on at least a pair of detection objects that are separated acoustically from each other, a sound wave signal transmitted from the detecting unit is transmitted to each of the pair of detection objects alternately to be relayed to the terminal unit via the relay unit, returned sound wave from the terminal unit are transmitted to each of the pair of detection objects alternately to be sent to the detecting unit via the relay unit, and also a sound wave signal is transmitted from the detecting unit to each of the pair of detection objects alternately.

According to such a construction, by propagating sound wave to each of the pair of detection objects alternately, it is possible to propagate sound wave bypassing a break, and it is possible to receive reflected sound wave from the break with certainty, regardless of a location of break, so that it is possible to specify the location of break even in a case where respective units are arranged at maximum intervals between which signals can be transmitted.

BRIEF DESCRIPTION OF THE DRAWINGS

FIG. 19 is a block diagram of a sixth embodiment of the present invention.

FIG. 20A and FIG. 20B are explanatory diagrams of signal propagation operation, in the sixth embodiment.

FIG. 22 is a time chart at a time of signal propagation operation in FIG. 20B.

FIG. 23A and FIG. 23B are explanatory diagrams showing an example of signal propagation operation when there is a break, in the sixth embodiment.

FIG. 25 is a time chart at a time of signal propagation operation in FIG. 23B.

BEST MODE FOR CARRYING OUT THE INVENTION

As follows is a description of preferred embodiments of a failure detecting system according to the present invention, with reference to drawings.

Figure 2:
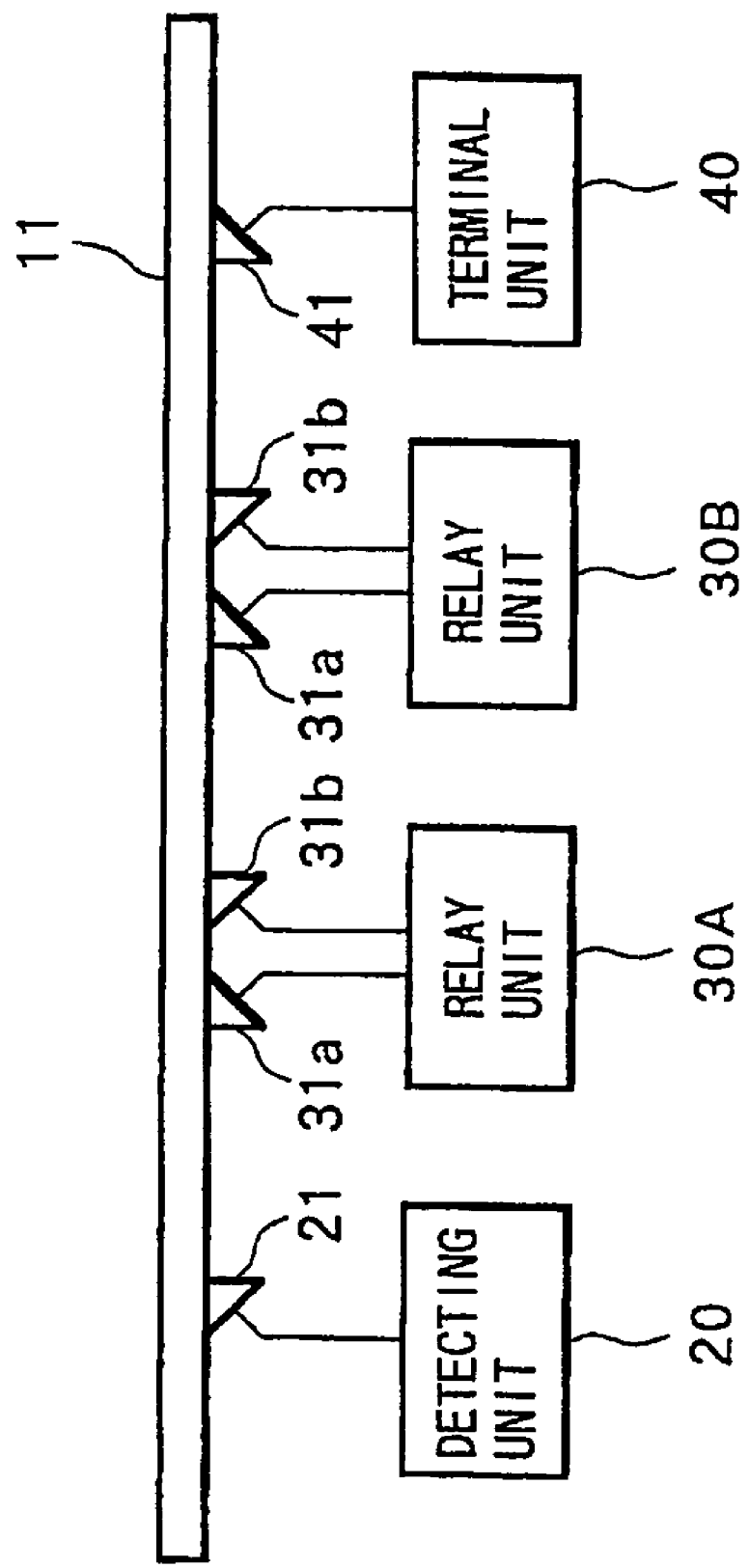
FIG. 2 is a block diagram showing a first embodiment of the present invention.

FIG. 2 shows a first embodiment of the present invention, and shows an example applied to a rail break detection.

In FIG. 2, along a break detection region of a rail 11, being a detection object, a detecting unit 20 is arranged at the start of the detection region and a terminal unit 40 is arranged at the end of the detection region. Furthermore, an appropriate number of relay units 30A and 30B (the present embodiment shows an example with two units arranged) is arranged at intervals in accordance with the length of the detection region. Here, needless to say, the number of relay units is not limited to two.

The detecting unit 20 is provided with an ultrasonic transducer 21 attached in contact with the rail 11, being a transmission medium, so as to be enable to transmit ultrasonic waves as sound wave to the direction of relay unit 30A, and to receive ultrasonic waves from the direction of relay unit 30A. Furthermore, based on transmission and reception information from transmitting and receiving circuits connected to the ultrasonic transducer 21 as described later, the detecting unit 20 judges whether or not there is a break, specifies the location of the break or the like, and transmits information of the judgment or specifying result to a central processing unit or the like (not shown in the figure) via a communication line.

The terminal unit 40 is provided with an ultrasonic transducer 41 attached in contact with the rail 11, so as to enable to transmit ultrasonic waves to the direction of relay unit 30B, and to receive ultrasonic waves from the direction of relay unit 30B. The ultrasonic transducer 41 is connected to internal transmitting and receiving circuits, which are not shown in the figure. The construction of the terminal unit 40 is such that when receiving ultrasonic waves transmitted by the relay unit 30B, it returns the ultrasonic waves to the relay unit 30B.

The relay units 30A and 30B each is provided with an ultrasonic transducer 31a, being a first transmission and reception section, attached in contact with the rail 11, so as to enable to transmit ultrasonic waves to a direction of detecting unit 20 and to receive ultrasonic waves from the direction of detecting unit 20, and an ultrasonic transducer 31b, being a second transmission and reception section, attached in contact with the rail 11, so as to enable to transmit ultrasonic waves to the direction of relay unit 30B (terminal unit direction) and to receive ultrasonic waves from the direction of the relay unit 30B (terminal unit direction). The construction of the relay unit 30A is such that when receiving ultrasonic waves transmitted by the detecting unit 20 at the ultrasonic transducer 31a, it transmits the ultrasonic waves to the relay unit 30B via the ultrasonic transducer 31b, and when receiving ultrasonic waves transmitted by the relay unit 30B at the ultrasonic transducer 31b, it transmits the ultrasonic waves to the detecting unit 20 via the ultrasonic transducer 31a. The relay unit 30B is constructed similarly. When receiving ultrasonic waves transmitted by the relay unit 30A at the ultrasonic transducer 31a, the relay unit 30B transmits the ultrasonic waves to the terminal unit 40 via the ultrasonic transducer 31b, and when receiving ultrasonic waves transmitted by the terminal unit 40 at the ultrasonic transducer 31b, it transmits the ultrasonic waves to the relay unit 30A via the ultrasonic transducer 31a.

Figure 3:
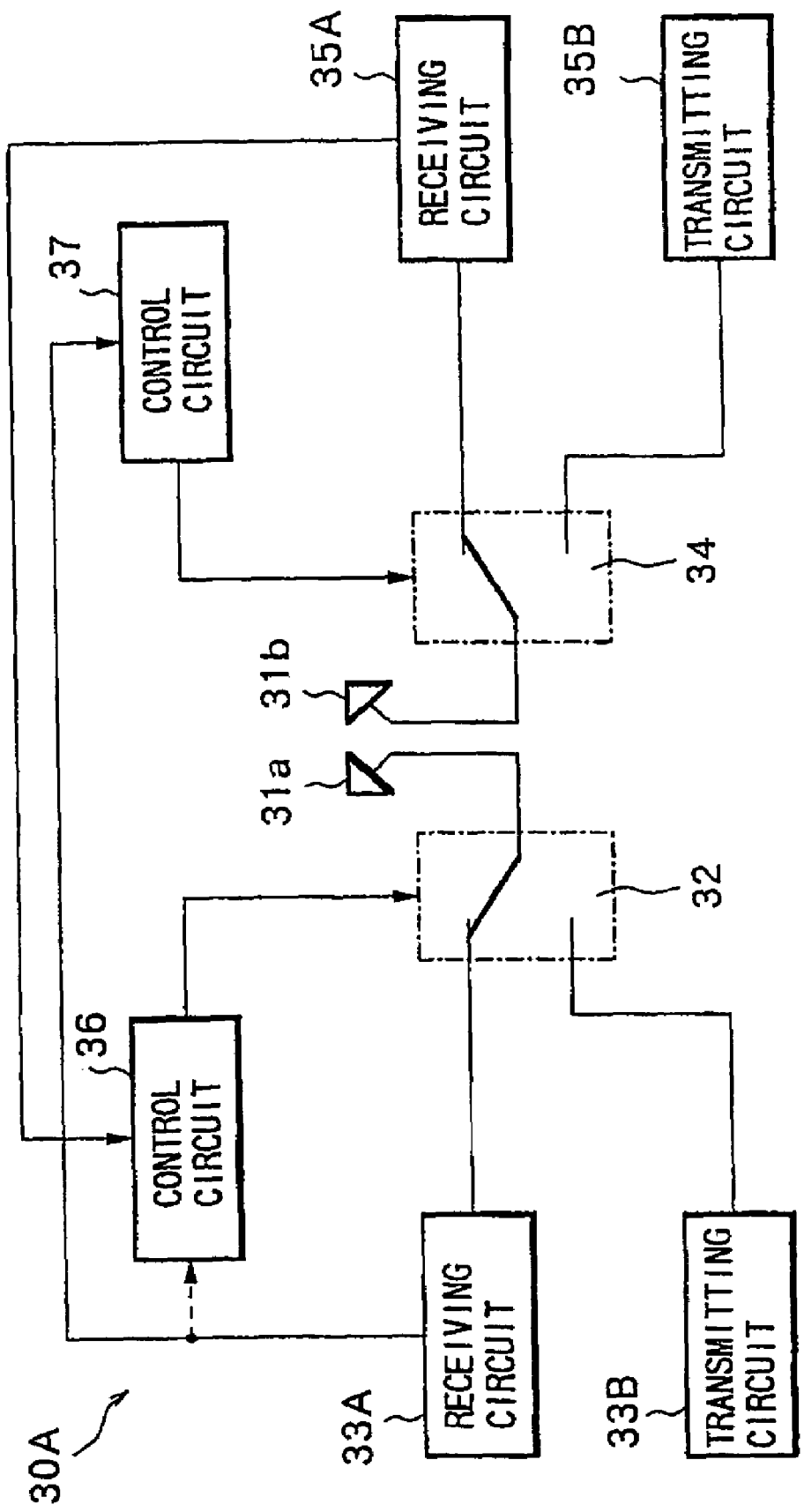
FIG. 3 shows a configuration example of a relay unit.

FIG. 3 shows a configuration example of the relay unit 30A. The relay unit 30B has the same construction, and its description is thus omitted.

In FIG. 3, the relay unit 30A comprises a receiving circuit 33A and a transmitting circuit 33B that can be connected selectively to the ultrasonic transducer 31a via a change-over switch 32, a receiving circuit 35A and a transmitting circuit 35B that can be connected selectively to the ultrasonic transducer 31b via a change-over switch 34, and control circuits 36 and 37 that switching control the change-over switches 32 and 34, respectively, based on information indicative of the signal reception from the receiving circuits 35A and 33A.

Figure 4:
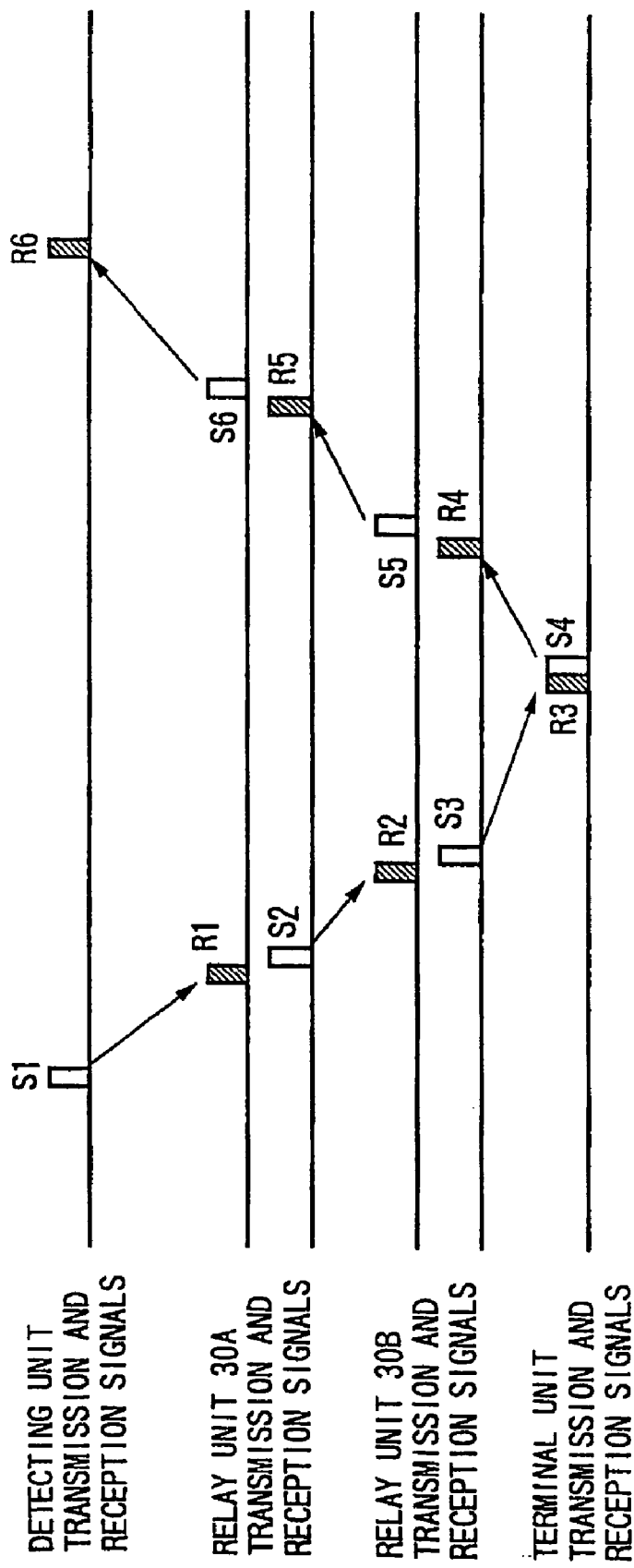
FIG. 4 is an operation time chart at a time of normal operation, in the first embodiment.
Figure 5:
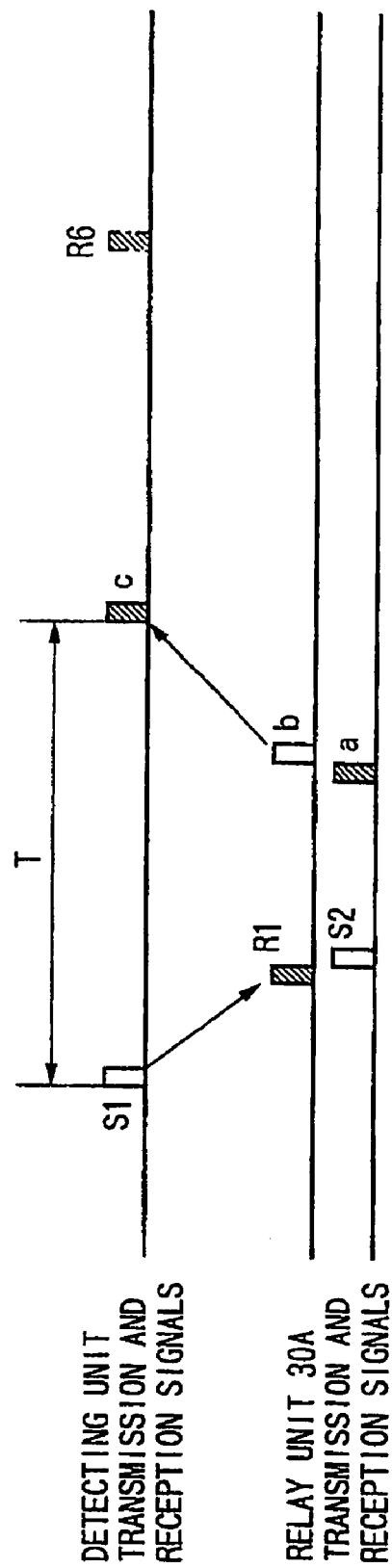
FIG. 5 is an operation time chart for when there is a break, in the first embodiment.

Next is a description of operation of the first embodiment with reference to time charts in FIG. 4 and FIG. 5. FIG. 4 shows a time chart for a case where the rail is normal, and FIG. 5 is a time chart for a case where there is a break between the relay unit 30A and the relay unit 30B.

Firstly, there will be described the operation during normal status, where there is no break in the rail 11.

The detecting unit 20 transmits ultrasonic waves to the direction of the relay unit 30A at a predetermined period. A signal S1 transmitted from the detecting unit 20 is received by the ultrasonic transducer 31a of the relay unit 30A, and a reception signal R1 is generated. When the receiving circuit 33A receives the signal R1, the relay unit 30A outputs information indicative of the signal reception to the control circuit 37. Based on the information indicative of the signal reception, the control circuit 37 switches the change-over switch 34 to the transmitting circuit 35B side. In this manner, ultrasonic waves are transmitted to the relay unit 30B via the ultrasonic transducer 31b. Accordingly, the transmission signal S1 from the detecting unit 20 is relayed as a signal S2 by the relay unit 30A, to be transmitted to the direction of the relay unit 30B. Similarly, the transmission signal S2 from the relay unit 30A is received by the ultrasonic transducer 31a of the relay unit 30B, and a reception signal R2 is generated. The reception signal R2 is relayed as a transmission signal S3 by the relay unit 30B, to be transmitted to the terminal unit 40. The terminal unit 40 receives the signal S3, generates a transmission signal S4 due to the generation of a reception signal R3, to send the transmission signal S4 to the direction of the relay unit 30B. The transmission signal S4 is received by the relay unit 30B, and relayed as a transmission signal S5 due to the generation of a reception signal R4. The signal S5 is received by the relay unit 30A, and relayed as a transmission signal S6 due to the generation of a reception signal R5. The signal S6 is received by the detecting unit 20, and a reception signal R6 is generated.

In this manner, if there is no break in the rail 11, the signal S1 transmitted from the detecting unit 20 is relayed by the relay units 30A and 30B, to be transmitted to the terminal unit 40. An ultrasonic wave signal returned as information indicative of the signal reception from the terminal unit 40 is transmitted to the detecting unit 20 via the relay units 30A and 30B, so that the reception signal R6 is generated in the detecting unit 20. Since it is possible to calculate in advance the time for the ultrasonic wave signal to go forth and back between the detecting unit 20 and the terminal unit 40 via the rail 11, it is possible to set in advance the generation time of the reception signal R6 in the detecting unit 20 when the rail 11 is normal. Accordingly, by setting a time range in advance based on a predicted generation time in the detecting unit 20, and by monitoring whether or not the reception signal R6 is generated within the preset time range, it is possible to monitor whether or not there is a break, and hence if the signal R6 is generated within the set time range, the rail 11 can be judged to be normal.

Next is a description of the case where the rail 11 has a break with reference to the time chart in FIG. 5.

In the case where there is a break in the rail 11 between the relay units 30A and 30B, the transmission signal S2 from the relay unit 30A, based on the transmission signal S1 from the detecting unit 20, is reflected at the break. As a result, the relay unit 30A receives reflected waves from the break at the ultrasonic transducer 31b, and a reflected reception signal "a" is generated as shown in FIG. 5. When the signal "a" is generated, the relay unit 30A transmits a signal "b" to the detecting unit 20 via the ultrasonic transducer 31a by operations of the receiving circuit 35A, the control circuit 36 and the change-over switch 32. The detecting unit 20 generates a reception signal "c" on receiving the signal "b". The reception signal "c" which is based on the reflection from the break, becomes outside the set time range earlier than the generation time of the reception signal R6 (shown by dashed lines in FIG. 5). Hence, it is possible to judge that the reception signal "c" is generated by reflected waves from the break.

In the case where it is judged that the reception signal "c" is the one based on the break, in the detecting unit 20, it is possible to calculate a rail break location X from the equation X=C·T/2 where T is the time from the transmission of the signal S1 to the reception of signal "c" and C is the propagation speed of ultrasonic waves. Hence, it is possible to specify the break location. Information such as the abovementioned judgment of normal operation and the break location is transmitted to the central processing unit connected to the detecting unit 20 through the communication line, although not shown in the figure.

As above, in the first embodiment, it is monitored whether or not the reception signal R6 is generated due to a return signal from the terminal unit 40. If the signal R6 is generated, it is judged that the rail 11 is normal, and if the reception signal "c" is generated, it is judged that there is a break. Furthermore, if the detecting unit 20 does not receive a signal, it means that some abnormality has occurred in the ultrasonic wave transmission system.

Figure 6:
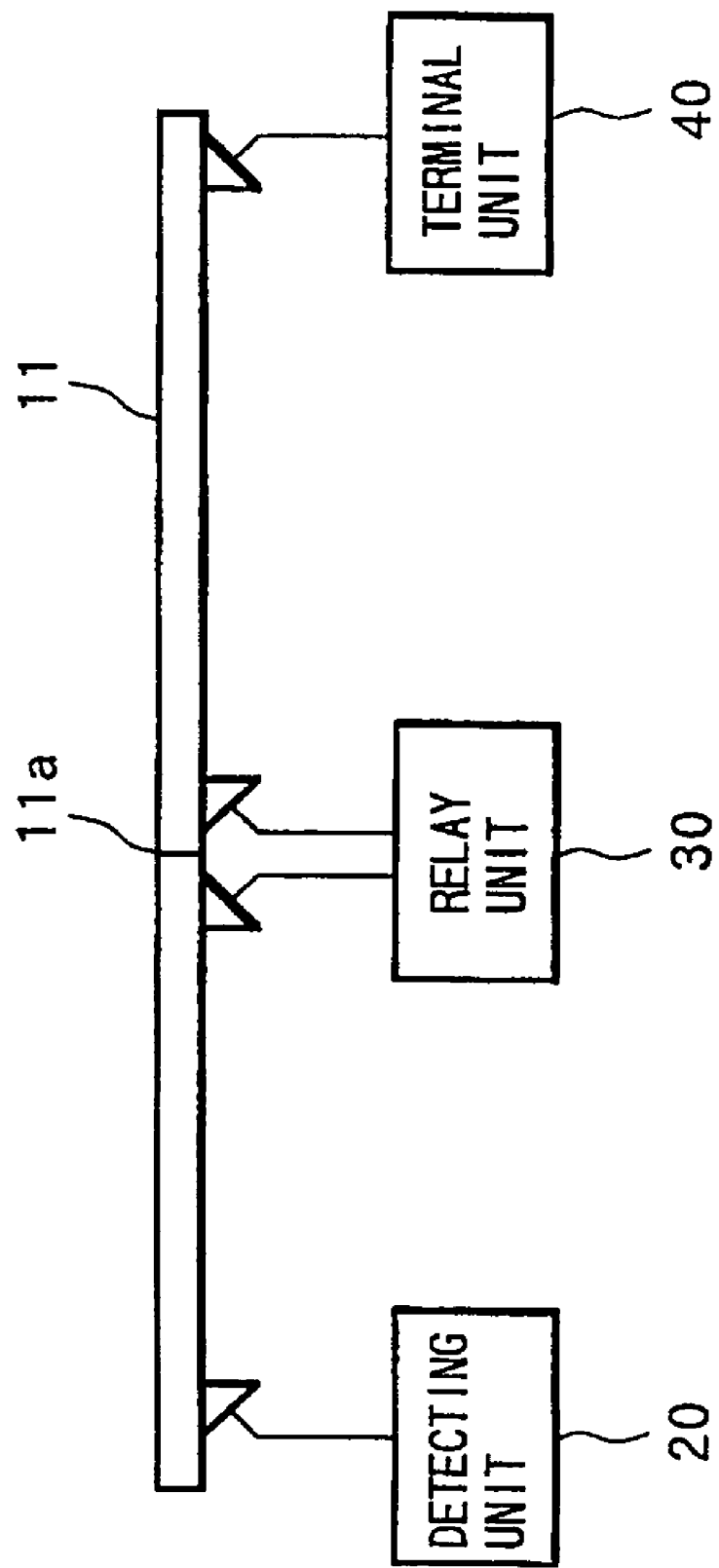
FIG. 6 shows the installation state of each unit when there is a joint in a rail.

In a case where there is a joint in the middle of the detection region of the rail 11, as shown in FIG. 6, the two ultrasonic transducers of the relay unit 30 may be installed on the rail 11 so as to cross over a joint 11a. If there is the joint 11a in the detection region, there is a reflected wave from the joint 11a. However, if the reception signal R6 is generated based on the transmission from the terminal unit 40, it is judged that the rail is normal.

Figure 7:
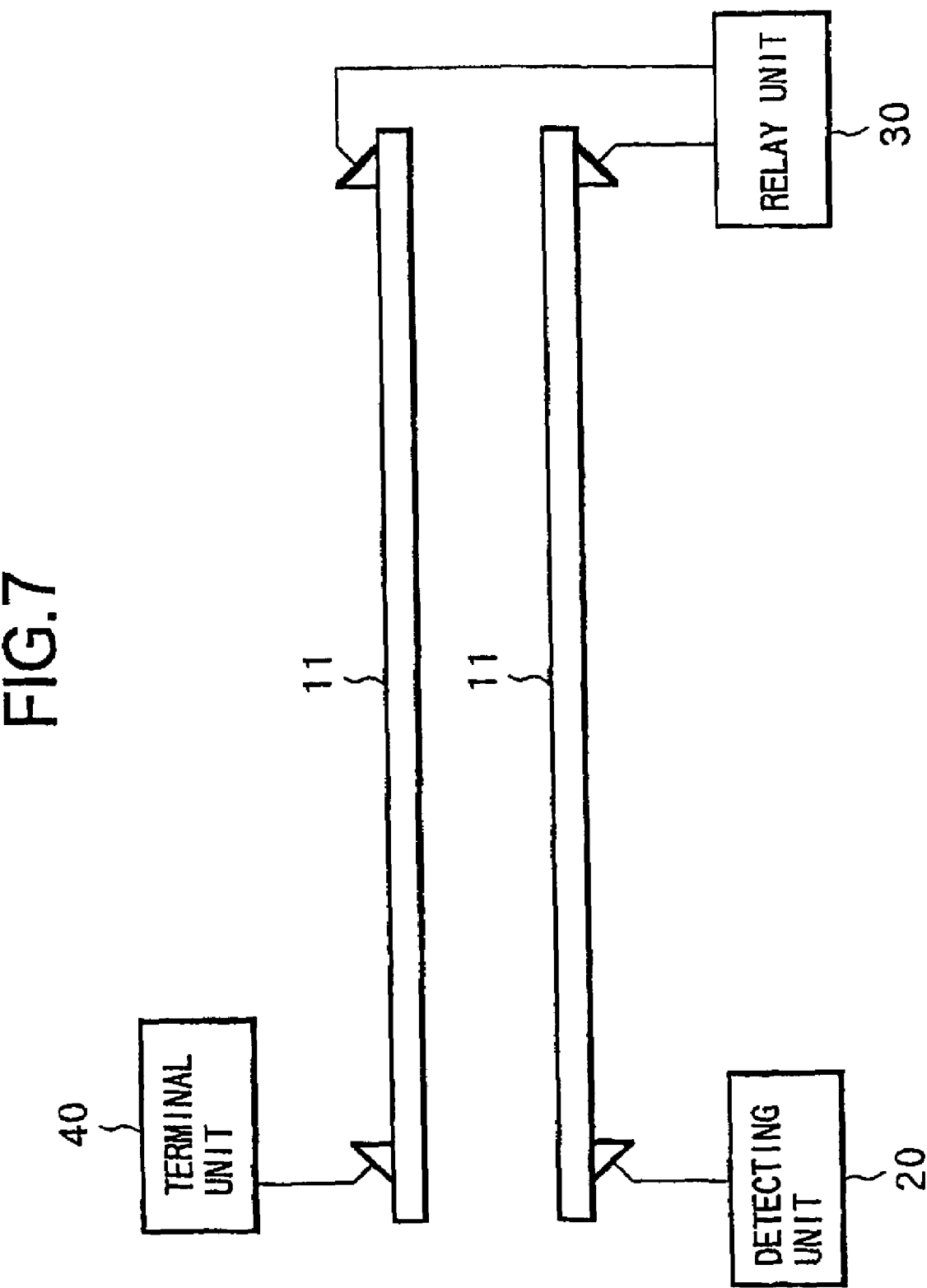
FIG. 7 shows the installation state of each unit when breaks in a pair of rails are checked at the same time.

Furthermore, in a case where breaks in a pair of rails 11 are monitored at the same time, then as shown in FIG. 7, the detecting unit 20 may be arranged on one of the rails and the terminal unit 40 may be arranged on the other rail, at one end of the detection region of the rails 11, and also the relay unit 30 may be arranged at the other end of the detection region so that the two ultrasonic transducers are installed across both rails.

Here, in the case where the constructions are as in FIG. 6 and FIG. 7, the transmission operation of ultrasonic wave signals is similar to the case in FIG. 2. Therefore, the description is omitted.

In the case of the first embodiment described above, when the number of relay units 30 is increased, the cumulative time of a time delay from the reception of signal to the transmission of signal in each relay unit 30 is increased, and hence the error in the reception time of the reflected signal "c" from the break is increased. Therefore, there is a possibility that the accuracy of detecting the location of a break is reduced.

Next is a description of a second embodiment of the present invention that can detect the location of a break accurately regardless of the number of relay units.

When a signal is received from the direction of detecting unit, each relay unit of the present embodiment relays and transmits the signal to the direction of terminal unit, and also transmits it back to the direction of detecting unit via an ultrasonic transducer 31a. In this case, the construction may be such that each relay unit also outputs information indicative of the signal reception from the receiving circuit 33A to the control circuit 36, as shown by the broken line in FIG. 3. The constructions of the detecting unit and the terminal unit are similar to the first embodiment.

Figure 8:
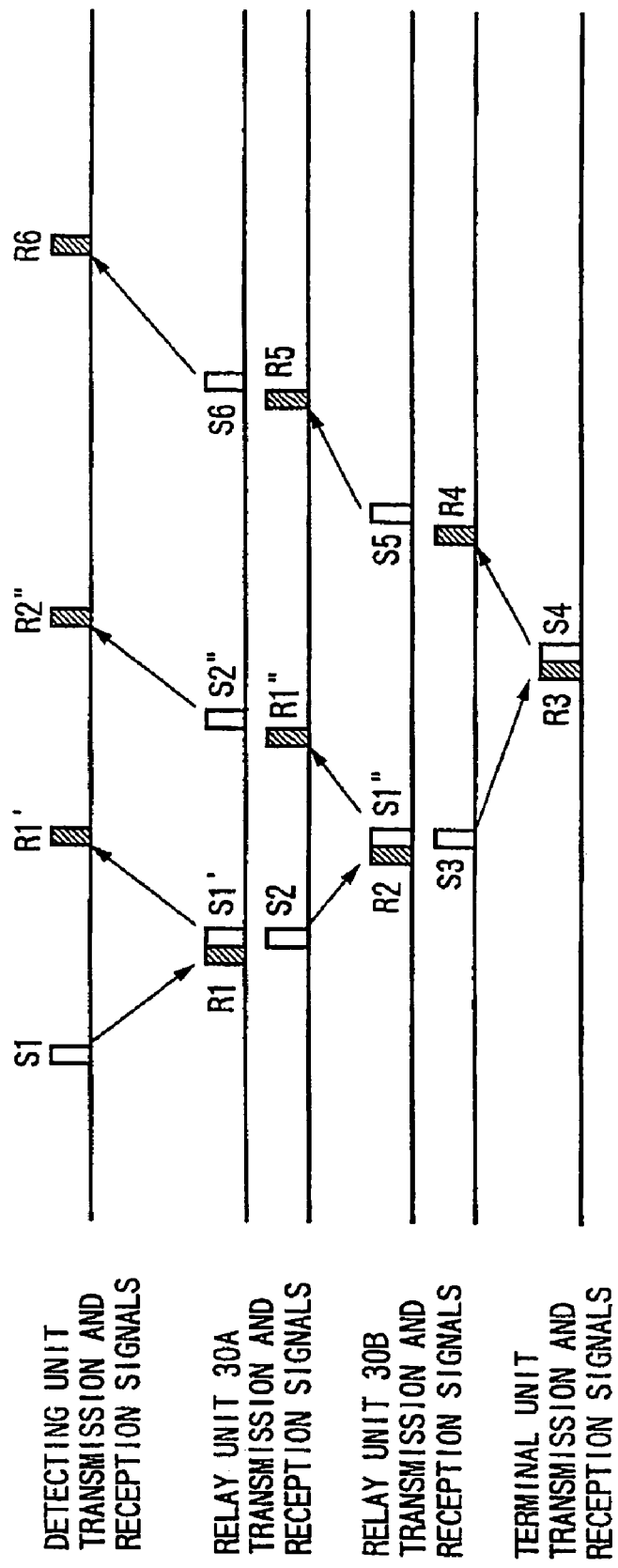
FIG. 8 is an operation time chart at a time of normal operation, in a second embodiment of the present invention.
Figure 9:
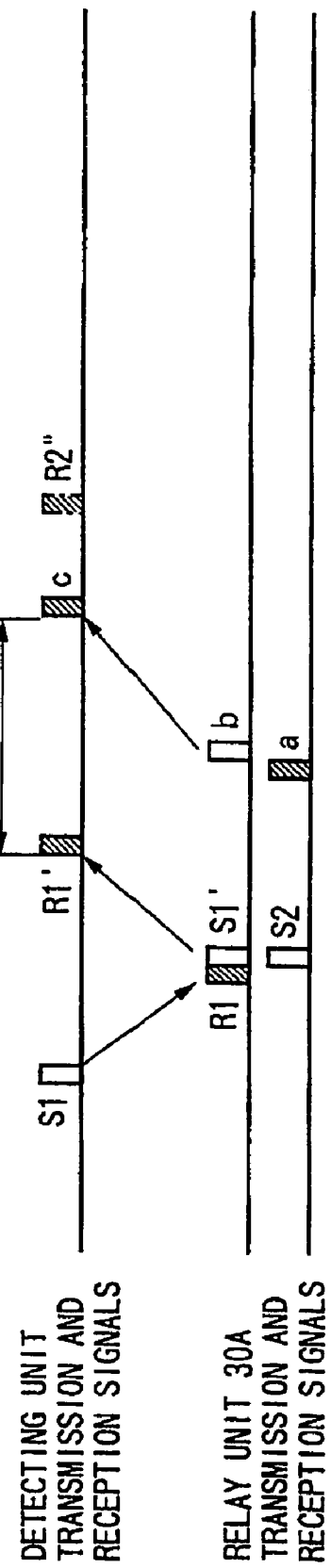
FIG. 9 is an operation time chart for when there is a break, in the second embodiment.

Next is a description of operations of the second embodiment with reference to operation time charts in FIG. 8 and FIG. 9. The description hereunder assumes that the detecting unit, relay unit and terminal unit are arranged similarly to those in the first embodiment as shown in FIG. 2. In the figures, the same symbols are used for the same items as in FIG. 4 and FIG. 5.

FIG. 8 is an operation time chart in a normal case where there is no break in the rail 11. In FIG. 8, on receiving a signal S1, the relay unit 30A generates a reception signal R1 and transmits ultrasonic waves to the relay unit 30B as a signal S2, similarly to the first embodiment, and at the same time also, as shown in the figure, transmits it as a signal S1' to the detecting unit 20. On receiving the signal S2, the relay unit 30B generates a reception signal R2 and transmits ultrasonic waves to the terminal unit 40 as a signal S3, and at the same time, as shown in the figure, transmits it as a signal S1" to the relay unit 30A. On receiving the signal S1", the relay unit 30A generates a signal R1", and transmits it to the detecting unit 20 as a signal S2". In the case where the rail 11 is normal, as shown in the figure, the detecting unit 20 generates reception signals R1' and R2' based on the transmission signals S1' and S1" from the relay units 30A and 30B, and the reception signal R6 based on the transmission signal S4 from the terminal unit 40, similarly to the first embodiment. Accordingly, if the reception signal R6 is generated within a set time range, the detecting unit 20 can judge that the rail is normal.

Next is a description of a case where the rail has a break using the time chart in FIG. 9.

In the case where there is a break between the relay units 30A and 30B in the rail 11, the relay unit 30A generates normally the transmission signals S2 and S1' similarly to FIG. 8 due to the generation of the reception signal R1, and the reception signal R1' is generated in the detecting unit 20. The transmission signal S2 of the relay unit 30A is reflected by the break, a signal "b" is transmitted from the relay unit 30A to the detecting unit 20 based on a reflected reception signal "a", and the detecting unit 20 generates a reception signal "c" based on the reflected waves earlier than the time when the reception signal R2" is generated at normal times. In the present embodiment, in this case, time T when the signal "c" is received is measured with the time when the reception signal R1' is generated as a reference, and the location of the break in the rail is calculated from this time T and the propagation speed C. In this manner, it is possible to eliminate an influence of delay time between the reception of signal and the transmission of signal in each relay unit 30, and also it is possible to specify the location of a break more accurately than in the first embodiment.

Furthermore, in the second embodiment, it is possible to compensate for a propagation speed C of ultrasonic waves using the transmission signal S1' of the relay unit 30A.

That is to say, if a distance between the detecting unit 20 and the relay unit 30A is L, then the time "to" from when the signal S1 is generated by the detecting unit 20 to when the reception signal R1' is generated is represented by "to"=2L/C+tx. Here, "tx" represents a time delay from when the relay unit 30A receives ultrasonic waves to when it transmits them, which is a fixed value, being fixed by the design. If the time "to" is measured in accordance with the above-described equation, the propagation speed C at that time can be calculated. In this manner, since it is possible to correct the propagation speed C of the ultrasonic waves, if the corrected propagation speed C is used for detecting the location of a break, it is possible to specify the location of a break more accurately.

Furthermore, in the case of the second embodiment, as shown in the time chart of FIG. 8, since the reception signals corresponding to the number of relay units between the detecting unit and terminal unit are generated in the detecting unit 20, then by counting the number of generated reception signals, the number of relay units installed can be monitored sequentially on the side of the detecting unit 20. Therefore, by checking the number of signals to be received and the reception times on the side of the detecting unit 20, it is possible to monitor the operating status of all of the relay units 30 and the terminal unit 40.

Moreover, in the construction of the second embodiment, if there is a break in the rail, the detecting unit does not receive transmission signals from the relay units and the terminal unit positioned behind the break. Therefore, by monitoring the number of reception signals in the detecting unit 20, it is possible to detect whether or not there is a break and the approximate location of the break.

In the case where there is a break between the last relay unit and the terminal unit, it is not possible to detect whether there is a break from the number of reception signals. In this case, it may be judged whether the reception signal is caused by the reflection wave at the break based on the time that the final reception signal was generated or is caused by the return signal from the terminal unit.

Furthermore, in the construction of the present invention, by setting the levels of the ultrasonic wave transmissions in the direction of detecting unit of each relay unit 30 and the terminal unit 40 appropriately, it is possible to monitor whether or not the functions for receiving reflected waves from the break are normal in the detecting unit 20 and the relay units 30.

Figure 10:
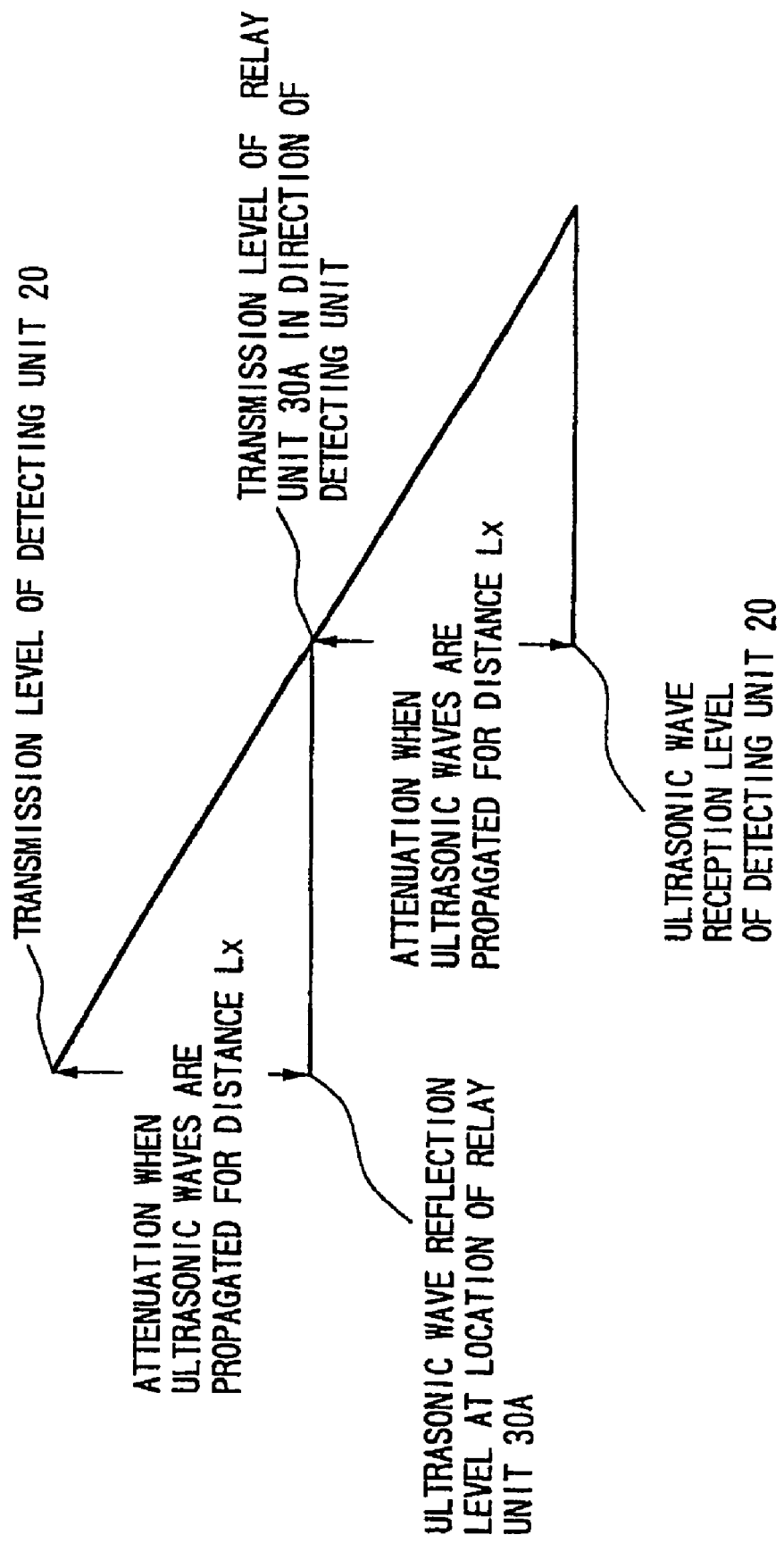
FIG. 10 is an explanatory diagram of the principle of a reflected sound wave reception function checking of a unit.

Such a monitoring function will be described in FIG. 10 using the transmitting and receiving operation between the detecting unit 20 and the relay unit 30A as an example.

It is assumed that a distance between the detecting unit 20 and the relay unit 30A is Lx. A transmission signal from the detecting unit 20 is attenuated before it reaches the location of the relay unit 30A, which is the distance Lx away, and after reached, it is further propagated the distance Lx while being attenuated, to be received by the detecting unit 20. Therefore, the reception ability of the detecting unit 20 is set so as to enable to detect reflected waves generated at the maximum distance Lx, that is, the location of the relay unit 30A. To check whether or not the detecting unit 20 has an ability to receive reflected waves generated at the location of the relay unit 30A, the arrangement may be such that, as shown in FIG. 10, the transmission level from the relay unit 30A to the detecting unit 20 is sufficiently lower than the transmission level of the detecting unit 20, in the direction of relay unit 30A, that is, almost the same level as the reflected waves at the location of the relay unit 30A. Here, to check the reflected wave reception function of the other relay units, the level of transmissions to the direction of detecting unit in the adjacent relay unit and the terminal unit may be set similarly.

In this manner, it is possible to monitor whether or not the reflected wave reception functions in the detecting unit 20 and the relay unit 30 are normal, at the same time as the break detection operation, and hence the reliability of the failure detecting system is improved.

Each of the above-described embodiments shows a configuration example in which sound wave is propagated to be relayed through the transmission medium in one direction from the detecting unit side to the terminal unit side, and alternatively from the terminal unit side to the detecting unit side. As follows is a description of a configuration example for a case where sound wave is propagated in bi-directions through the transmission medium.

Figure 11:
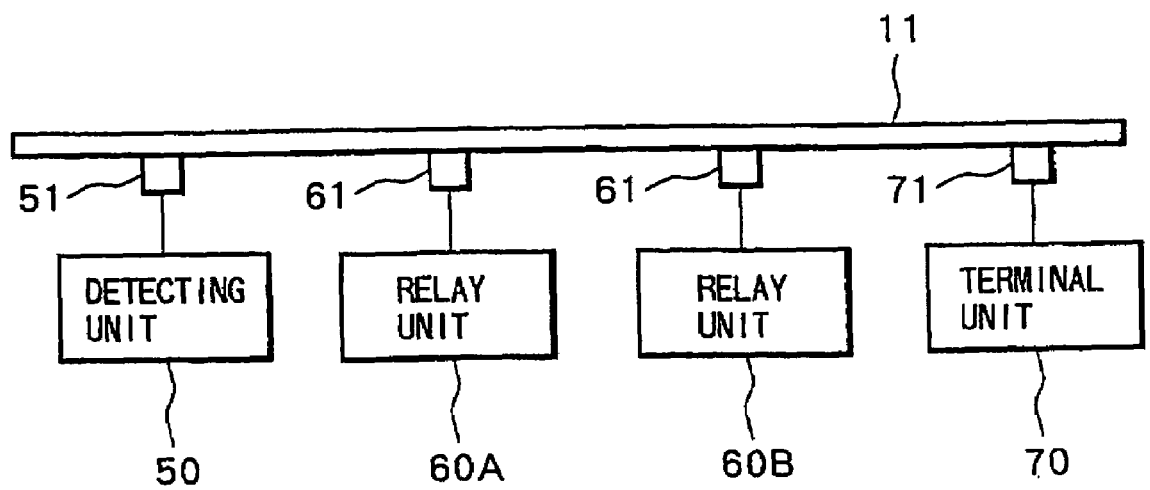
FIG. 11 shows a third embodiment of the present invention, and is a block diagram of a case where sound wave is propagated in bi-directions.

FIG. 11 shows a third embodiment of the present invention in which sound wave is propagated in bi-directions through the transmission medium.

In FIG. 11, a detecting unit 50, relay units 60A and 60B, and a terminal unit 70, which are arranged along a break detection region of the rail 11, being the transmission medium, have ultrasonic transducers 51, 61 and 71, respectively, as their transmission and reception sections. The ultrasonic transducers 51, 61 and 71 of the units 50, 60 and 70 are mounted, respectively, such that the ultrasonic wave transmission and reception faces thereof are almost at right angles to the propagation direction of the rail 11, being the transmission medium. In this manner, ultrasonic waves as sound wave, transmitted from each of the ultrasonic transducers 51, 61 and 71, are propagated in bi-directions through the rail 11, the right and left directions in the figure.

The detecting unit 50, which has the same construction as the detecting unit 20, judges whether or not there is a break, specifies the location of the break or the like, based on transmission and reception information of the ultrasonic waves, and transmits information of the result to a central processing unit or the like (not shown in the figure) via a communication line.

The terminal unit 70 is constructed to, when receiving a transmission signal from the relay unit 60B, transmit an ultrasonic wave signal that is different from the transmission signal from the detecting unit 50 in order to distinguish it from the transmission signal from the detecting unit 50. A different signal means a signal whose generation time is differentiated by varying the number of pulses for example. Furthermore, The terminal unit 70 stops relay operation after the transmission, that is to say, does not perform an operation in which a signal is transmitted whenever received.

Figure 12:
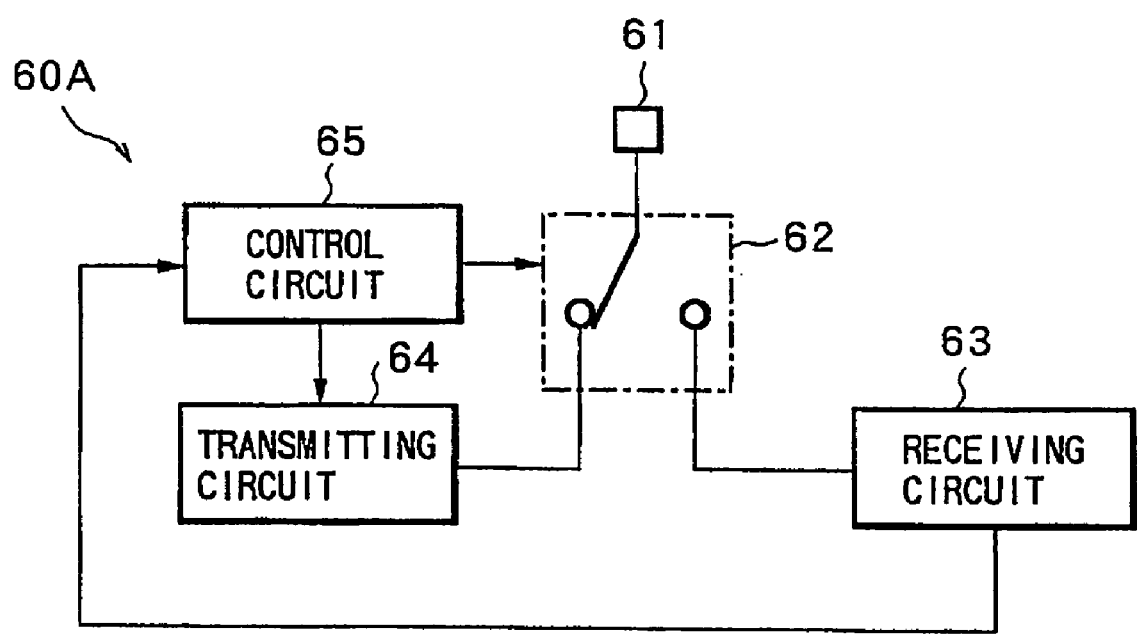
FIG. 12 shows a configuration example of a relay unit in the third embodiment.

The relay units 60A and 60B have the same construction, and have, as shown in FIG. 12, a receiving circuit 63 and a transmitting circuit 64, which can be selectively connected to the ultrasonic transducer 61 via a change-over switch 62, and a control circuit 65, which switching controls the change-over switch 62 based on information that a signal has been received from the receiving circuit 63 and information of the reception signal form, and also controls the transmission mode of the transmitting circuit 64.

That is to say, in each of the relay units 60A and 60B, when a signal is received, the change-over switch 62 is switched to the transmitting circuit 64 side by the control circuit 65 to transmit a signal, and thereafter is returned to the receiving circuit 63 side. Then, if the received signal is a signal from the detecting unit 50, a signal identical to the signal from the detecting unit 50 is transmitted, while if the received signal is a signal from the terminal unit 70, a signal identical to the signal from the terminal unit 70 is transmitted. After transmitting the signal identical to the signal from the terminal unit 70, the relay operation is stopped, and the transmission operation is not performed even if a signal is received.

A signal relay operation in the third embodiment will be described with reference to a time chart in FIG. 13. Here, the white squares in the figure indicate signals identical to those from the detecting unit 50, and the black squares indicate signals identical to those from the terminal unit 70.

The detecting unit 50 transmits an ultrasonic wave signal S1 in a predetermined cycle. A reception signal R1 is generated in the relay unit 60A due to the signal S1, and the relay unit 60A transmits a signal S2 identical to the signal S1. Since the signal S2 is propagated in bi-directions through the rail 11, reception signals R' and R2 are generated in the detecting unit 50 and the relay unit 60B, respectively, as shown in the figure. The relay unit 60B transmits a transmission signal S3 in response to the generation of the reception signal R2, and reception signals R2' and R3 are generated in the relay unit 60A and the terminal unit 70, respectively. Since the relay unit 60A transmits a transmission signal S2' in response to the generation of the reception signal R2', a reception signal R2" is generated in the detecting unit 50, and a reception signal R3' is generated in the relay unit 60B. Furthermore, the terminal unit 70 transmits a signal S4, which is different, for example in pulse numbers, from the signal S1 from the detecting unit 50, in response to the generation of the signal R3, and a reception signal R4 is generated in the relay unit 60B in response to this signal S4. The relay unit 60B transmits a signal S5 in response to the generation of the reception signal R4. The relay unit 60A transmits a signal S6 in response to the generation of the reception signal R5 due to the signal S5, and a reception signal R6 is generated in the detecting unit 50.

Here, since the terminal unit 70 stops the relay operation after transmitting the signal S4, then even if a reception signal R4' is generated due to the signal S5 from the relay unit 60B, it does not perform the transmission operation. Similarly, since the relay unit 60B also stops the relay operation after transmitting the signal S5 due to the signal S4 from the terminal unit 70, even if a reception signal R5' is generated by receiving the signal S6, it does not perform the transmission operation.

In this third embodiment, if the reception signal R6 is generated within a predetermined time range, the detecting unit 50 judges that the rail 11 is normal. In the case where there is a break in the rail 11, it is possible to detect the break similarly to the second embodiment as shown in FIG. 9. Furthermore, similarly to the second embodiment, since the same number of reception signals is generated in the detecting unit 50 as the number of relay units between the detecting unit and terminal unit, by counting the number of reception signals generated, the number of relay units installed can be sequentially monitored in the detecting unit 50. Therefore, by checking the number of reception signals and the reception times, it is possible to monitor the operating status of the relay units 60A and 60B and the terminal unit 70. It is easier to mount ultrasonic transducers on the transmission medium compared with the construction in which ultrasonic waves are propagated and relayed in a single direction through the transmission medium, and hence there is an advantage that there is no restriction in the mounting.

Figure 13:
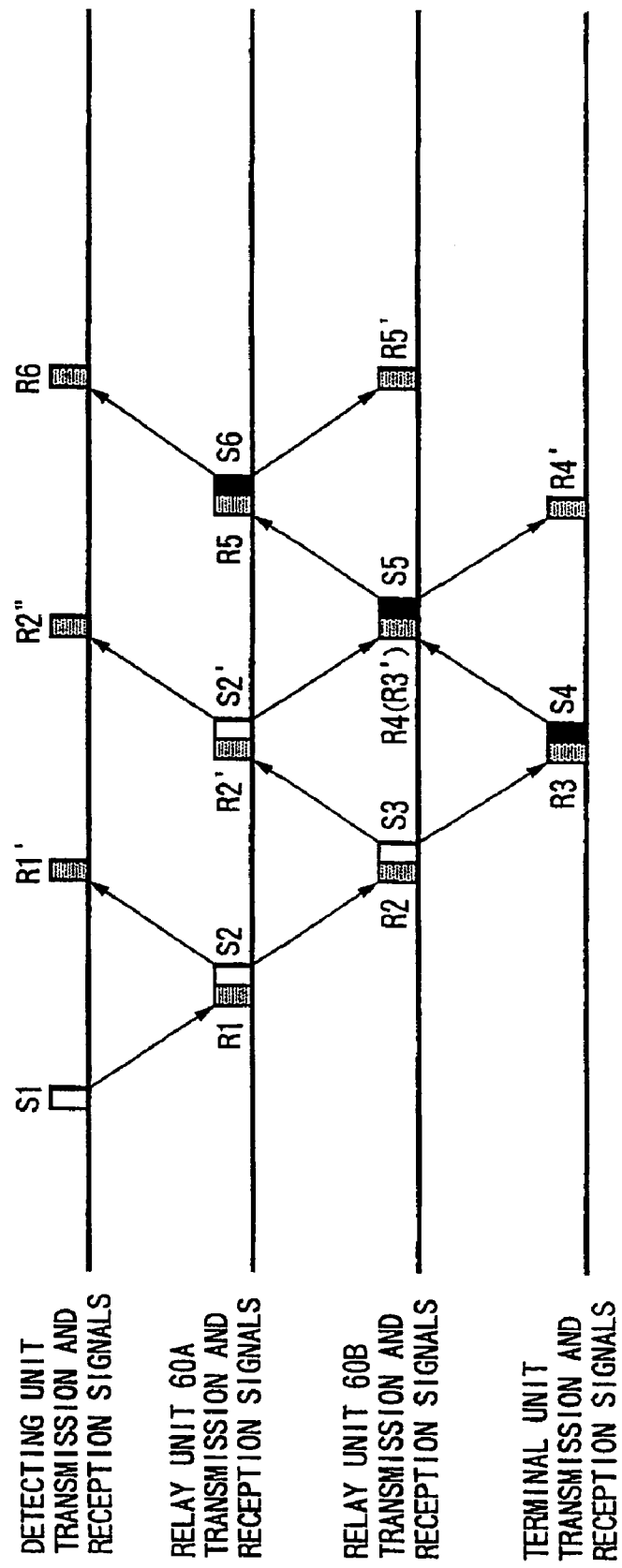
FIG. 13 is an operation time chart at a time of normal operation, in the third embodiment.

Incidentally, in the case of the third embodiment, as shown in FIG. 13, the transmission timing of the signal S4 from the terminal unit 70 and the transmission timing of the signal S2' from the relay unit 60A overlap with each other, so there is a possibility that the reception signals R4 and R3' interfere with each other in the relay unit 60B.

Next is a description of a fourth embodiment of the present invention, wherein the problem of reception signal interference as described above is avoided.

In the fourth embodiment, the transmission operation after receiving a signal is delayed in the relay operation of each relay unit, and a delay time is changed. To be specific, the construction is such that the delay time from when the relay unit receives a signal to when it transmits a signal is different between the first time it receives a signal and the second or later time it receives a signal. Furthermore, each relay unit has a construction to transmit a signal identical to a signal from the terminal unit when receiving reflected waves from a break.

Figure 14:
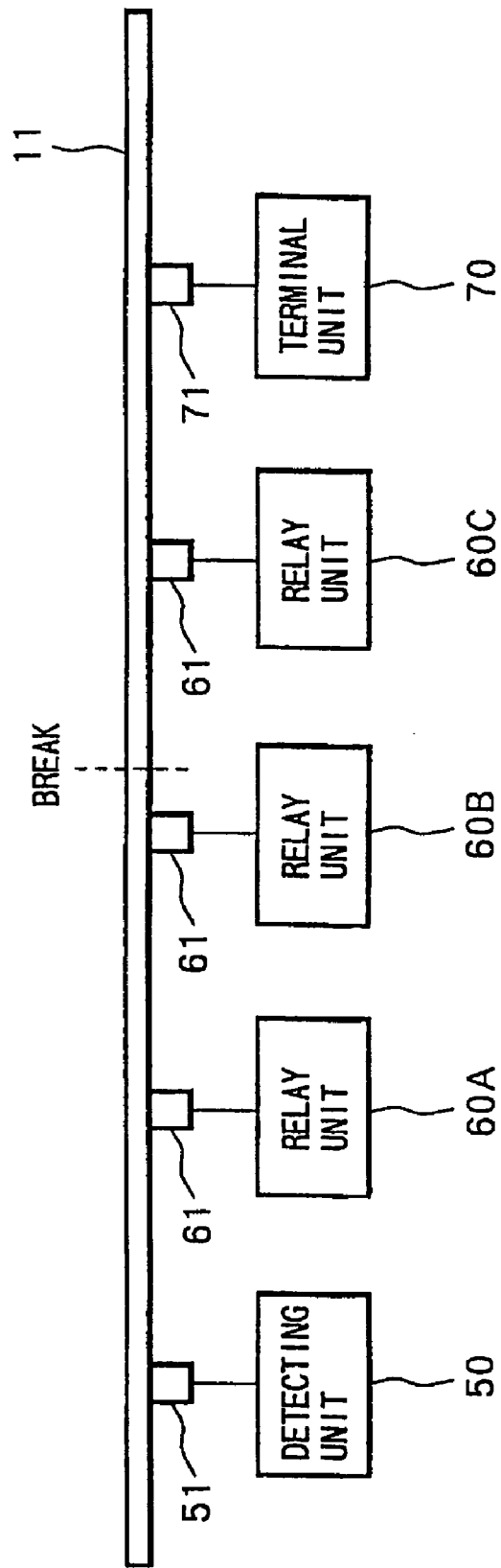
FIG. 14 is a block diagram of a fourth embodiment of the present invention.
Figure 15:
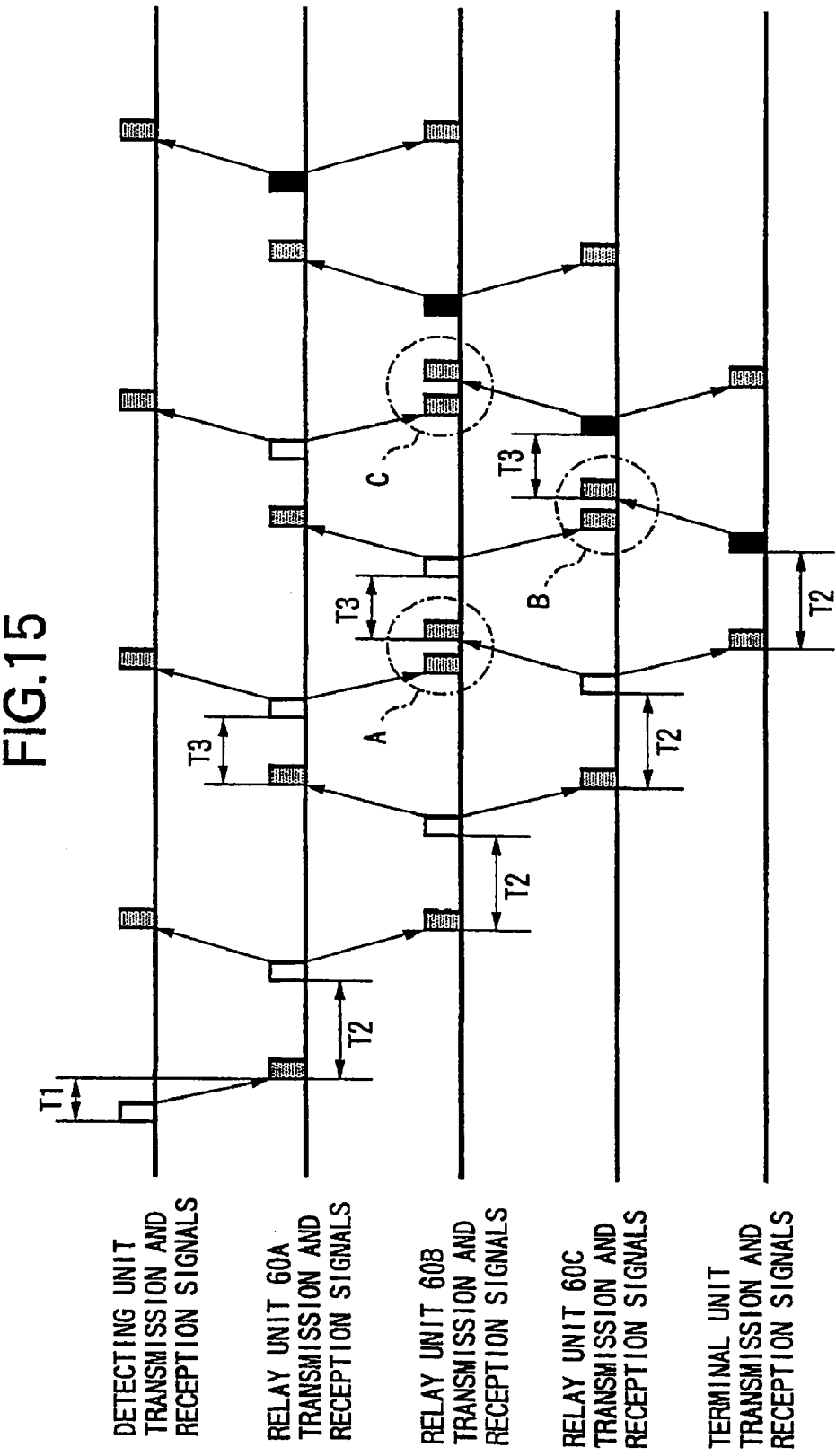
FIG. 15 is an operation time chart at a time of normal operation, in the fourth embodiment.

A signal transmission operation in the fourth embodiment will be described with respect to a case where three relay units 60A, 60B and 60C are provided as shown in FIG. 14 with reference to a time chart in FIG. 15. In FIG. 15, T2 designates a delay time of each of the relay units 60A through 60C when receiving a signal for the first time, and T3 designates a delay time when receiving a signal for a second or later time. T1 designates a signal propagation time between units.

As shown in FIG. 15, each of the relay units 60A through 60C transmits a signal after the lapse of time T2 from when receiving a first reception signal, and transmits a signal after the lapse of time T3 from when receiving a second or later time reception signal. Furthermore, the terminal unit 70 transmits a signal after the lapse of time T2 from when receiving a signal from the relay unit 60C. Relay operations other than changing the transmission timing are similar to the case of the third embodiment.

In such a construction, when the relay unit 60B receives a signal from the relay unit 60A and a signal from the relay unit 60C as shown in A and C of FIG. 15, and when the relay unit 60C receives a signal from the relay unit 60B and a signal from the terminal unit 70 as shown in B of FIG. 15, the reception timing of reception signals is delayed, and hence it is possible to prevent reception interference even in the case where ultrasonic waves are propagated in bi-directions.

Figure 16:
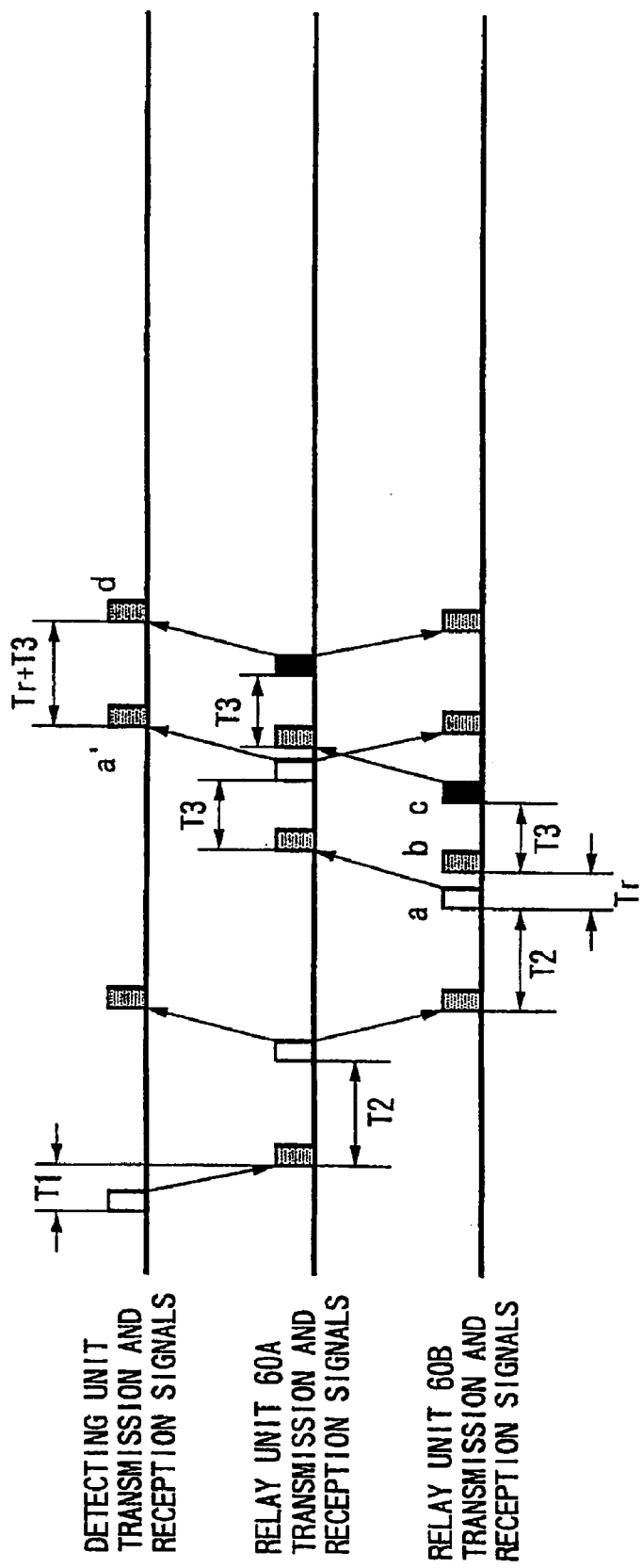
FIG. 16 is an operation time chart for when there is a break, in the fourth embodiment.

Next is a description of signal relay operation in the case where there is a break between the relay units 60B and 60C in the fourth embodiment, based on the time chart in FIG. 16.

In a case where there is a break between the relay units 60B and 60C, as shown by the broken line in FIG. 14, a transmission signal "a" from the relay unit 60B is reflected by the break, and a reception signal "b" is generated due to the reflected waves. The relay unit 60B transmits a signal "c" identical to a signal from the terminal unit 70 after the lapse of time T3 from when the reception signal "b" is generated. In response to the generation of this signal "c", a reception signal "d" based on the reflected waves is generated in the detecting unit 50 by the relay of the relay unit 60A. In the detecting unit 50, after a reception signal a' is generated based on the transmission signal "a" from the relay unit 60B, the reception signal "d" is generated with a delay of a time (Tr+T3). Here, the time Tr designates a time after the transmission signal "a" is generated from the relay unit 60B to when the reception signal "b" is generated due to the reflected waves.

Accordingly, in the detecting unit 50, in this case, by calculating the reception time (Tr+T3) of the signal "d" due to the reflected waves based on the time when the reception signal a' is generated, it is possible to detect that there is a break between the relay units 60B and 60C, at a location corresponding to a propagation time Tr/2, ahead of the relay unit 60B.

In the fourth embodiment, the construction is such that when receiving reflected waves, each of the relay units 60A through 60C transmits a signal identical to a signal from the terminal unit 70. However, the construction may be such that a signal different from the transmission signal from the detecting unit 50 and the transmission signal from the terminal unit 70 is transmitted.

Figure 17:
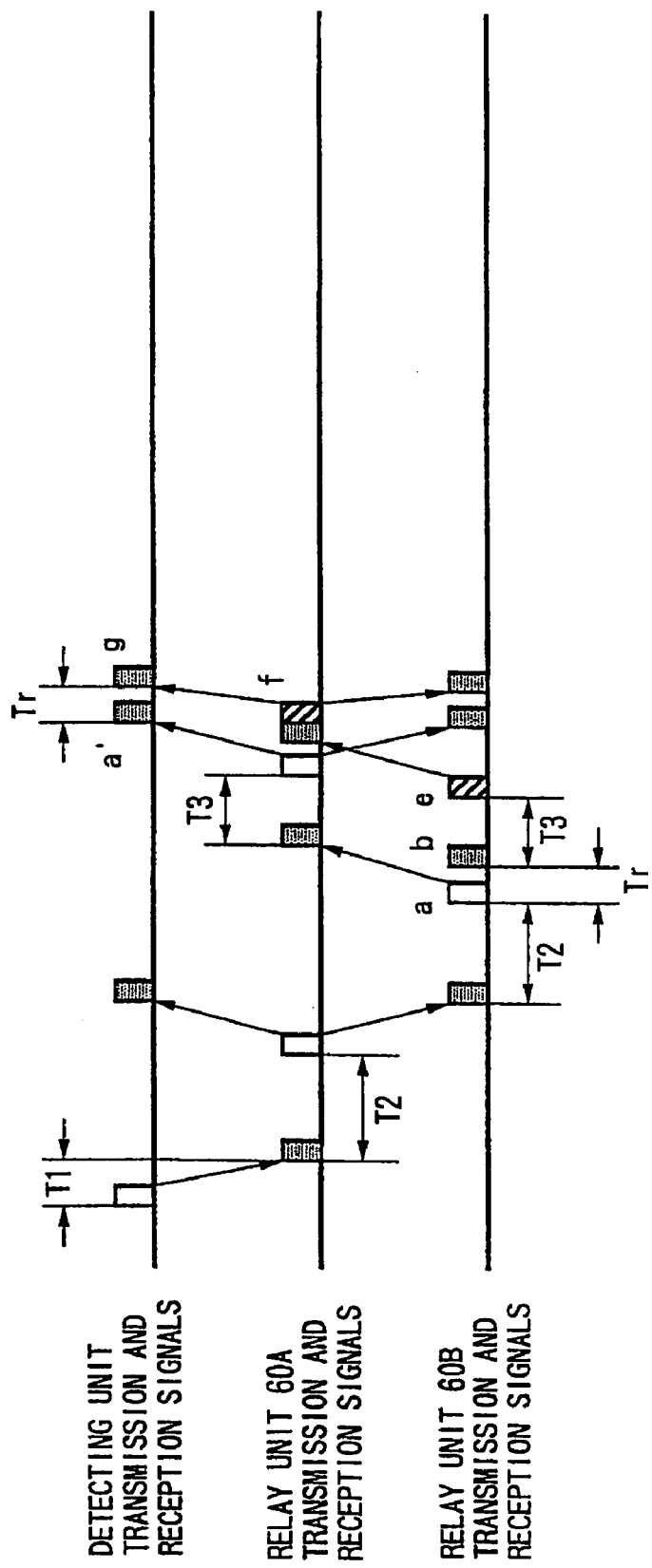
FIG. 17 is an operation time chart for when there is a break, in a fifth embodiment of the present invention.

FIG. 17 shows a time chart of signal relay operation in a fifth embodiment of the present invention with such a construction. The location of a break is the same as that in FIG. 14. Here, the fifth embodiment has a construction in which a signal is transmitted immediately after receiving reflected waves.

In FIG. 17, when a reflected wave reception signal "b" is generated based on a transmission signal "a", the relay unit 60B transmits a signal "e" of a kind different from the signal from the terminal unit 70 after the lapse of the time T3. On receiving this transmission signal "e", the relay unit 60A transmits a signal "f" without a delay. Accordingly, in the detecting unit 50, a signal "g" based on the signal "f" from the relay unit 60A is generated with the time delay Tr, after the reception signal a' is generated based on the transmission signal "a" from the relay unit 60B.

In such a construction, the detecting unit 50 can specify the location of a break by calculating the reception time Tr of the signal "g" due to the reflected waves based on the time when the reception signal a' was generated. Therefore, it is not necessary to use time T3, compared with the case of the fourth embodiment in FIG. 16, and hence the specifying operation of the break location becomes simplified.

Figure 18:
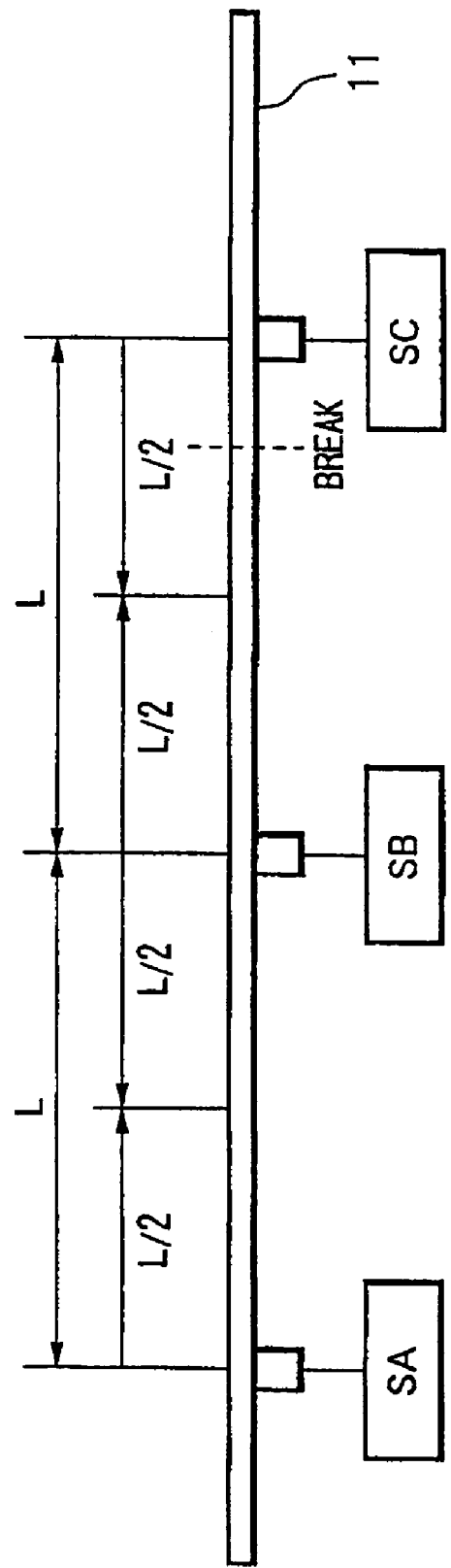
FIG. 18 is a diagram for explaining the relationship between sound wave transmission distance and reflected wave reception range in a case where respective units are arranged at maximum intervals between which signals can be transmitted.

Incidentally, if each unit is arranged at maximum interval over which a signal can be transmitted, it is possible to reduce the number of relay units as minimum as possible. That is to say, as shown in FIG. 18, each of units SA, SB and SC is arranged at the maximum interval L over which a signal can be transmitted. However, in the case where ultrasonic waves are transmitted bi-directions of a rail, even if the reflectance of a signal (ultrasonic wave) is assumed to be 100%, the range where each of the units SA, SB and SC can receive reflected waves is about half the distance L between units, that is, a distance range of L/2 from the location of each unit. Accordingly, if there is a break in the location shown by a broken line in the figure, for example, the unit SB cannot receive reflected waves from the break, and hence although the detecting unit can detect that there is a break because it does not receive a reception signal from the terminal unit, it cannot specify the location of the break.

FIG. 19 shows a sixth embodiment of the present invention, which can specify the location of a break regardless of the location of the break using the unit arrangement configuration as shown in FIG. 18.

The sixth embodiment has a construction in which at least a pair of transmission media, for example, a pair of rails 11A and 11B, are used as shown in FIG. 19, and by switching the transmission media through which sound wave is transmitted alternately, a signal is transmitted to a unit that can receive reflected waves from a break, so that the location of the break can be specified.

In FIG. 19, the detecting unit 50, the relay units 60A through 60C and the terminal unit 70 have two ultrasonic transducers each, 51A and 51B, 61A and 61B, and 71A and 71B, respectively. One set of ultrasonic transducers 51A, 61A and 71A is installed on the rail 11A side, and the other set of ultrasonic transducers 51B, 61B and 71B is installed on the rail 11B side. Furthermore, the constructions of the relay units 60A through 60C and the terminal unit 70 are the same as those shown by the solid lines in FIG. 3. Each ultrasonic transducer transmits ultrasonic waves when it receives a signal from the other ultrasonic transducer. Here, similar to the fourth embodiment, the signal generating state and the relay operation of each unit are such that signals generated by the detecting unit and terminal unit are different from each other. At a first time of receiving a signal, a signal is transmitted after the lapse of time T2, and at a second or later time of receiving a signal, a signal is transmitted after the lapse of time T3. Moreover, when receiving reflected waves from a break, the relay unit transmits a signal indicating that reflected waves have been received.

Signal relay operations of the present embodiment in the case where there is no break will be described based on FIG. 20.

In the sixth embodiment, the transmission operations of FIG. 20A and FIG. 20B are executed alternately. That is to say, the signal transmission operation from the ultrasonic transducer 51A of the detecting unit 50 is executed as in FIG. 20A, and then the signal transmission operation from the ultrasonic transducer 51B is executed as in FIG. 20B.

In FIG. 20A, after a transmission signal from the ultrasonic transducer 51A side is propagated to the terminal unit 70 in the order of solid line arrows A through D in the figure, a signal from the terminal unit 70 is propagated to the detecting unit 50 in the order of broken line arrows E through H in response.

Figure 21:
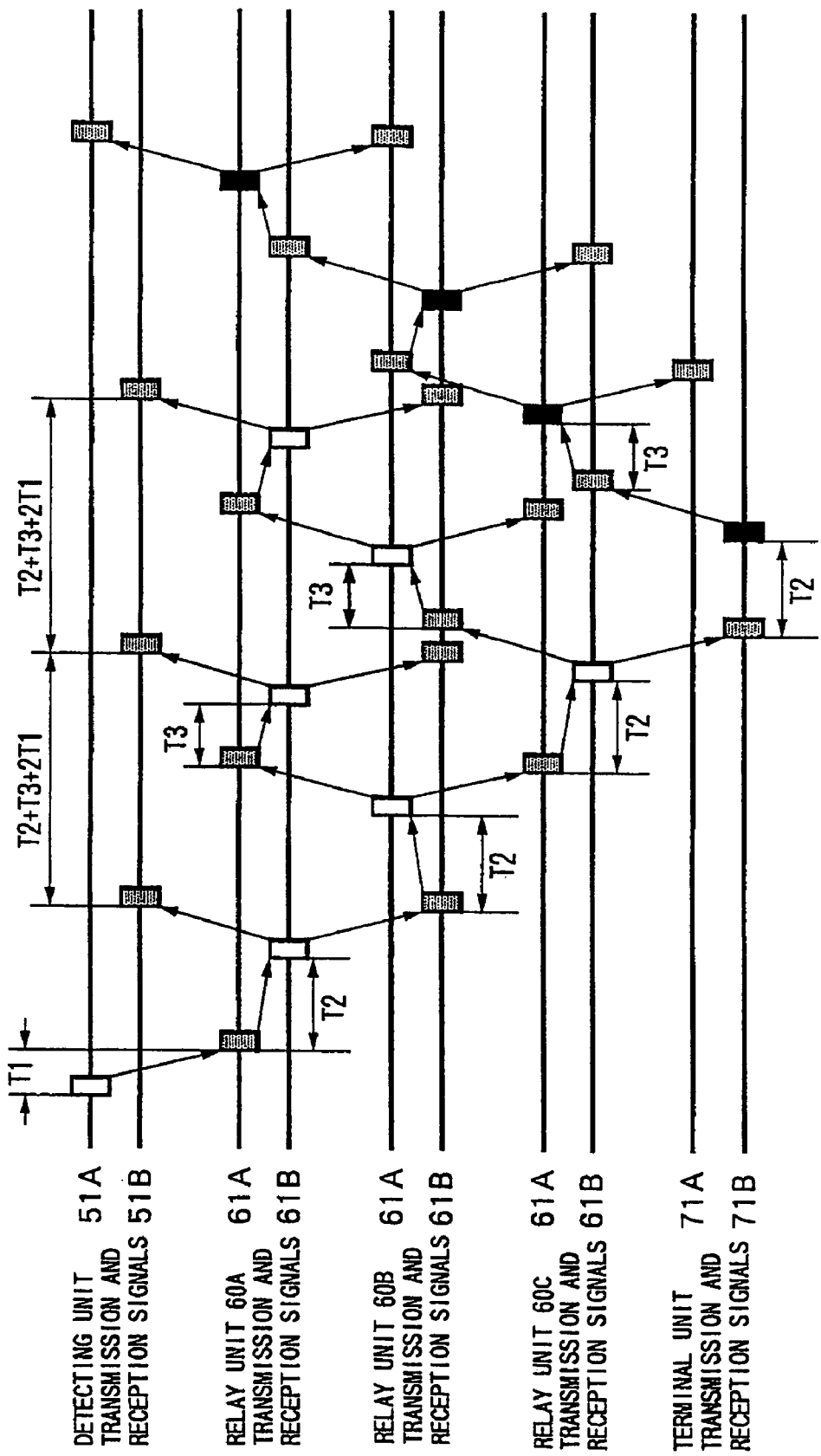
FIG. 21 is a time chart at a time of signal propagation operation in FIG. 20A.

That is to say, the transmission signal from the ultrasonic transducer 51A is propagated through the rail 11A as shown by the arrow A, to be received by the ultrasonic transducer 61A of the relay unit 60A, and a signal is transmitted to the other rail 11B from the ultrasonic transducer 61B of the relay unit 60A as shown by the arrow B, to be received by the ultrasonic transducer 61B of the relay unit 60B. Next, a signal is transmitted from the ultrasonic transducer 61A of the relay unit 60B to the rail 11A as shown by the arrow C, to be received by the ultrasonic transducer 61A of the relay unit 60C, and a signal is transmitted from the ultrasonic transducer 61B of the relay unit 60C to the rail 11B as shown by the arrow D, to be received by the ultrasonic transducer 71B of the terminal unit 70. On receiving the signal, the terminal unit 70 transmits a signal different from the signal from the detecting unit 50, from the ultrasonic transducer 71B to the rail 11B as shown by the arrow E. This signal is received by the ultrasonic transducer 61B of the relay unit 60C, and a signal is transmitted from the ultrasonic transducer 61A to the rail 11A as shown by the arrow F, to be received by the ultrasonic transducer 61A of the relay unit 60B. Next, a signal is transmitted from the ultrasonic transducer 61B of the relay unit 60B to the rail 11B as shown by the arrow G, to be received by the ultrasonic transducer 61B of the relay unit 60A. Next, a signal is transmitted from the ultrasonic transducer 61A of the relay unit 60A to the rail 11A as shown by the arrow H, to be received by the ultrasonic transducer 51A of the detecting unit 50. Thus, the signal from the terminal unit 70 is transmitted to the detecting unit 50 in response. FIG. 21 shows a detailed time chart for the transmitting and receiving operations of each unit in the case of FIG. 20A.

When the operations in FIG. 20A are completed, the signal transmission operations in FIG. 20B are executed. In FIG. 20B, after a transmission signal from the ultrasonic transducer 51B side of the detecting unit 50 is propagated to the terminal unit 70 in the order of solid line arrows A' through to D' in the figure, a signal is propagated from the terminal unit 70 to the detecting unit 50 in the order of broken line arrows E' through H' in response. The transmission operations in FIG. 20B and FIG. 20A are the same except that the transmitting and receiving order of each ultrasonic transducer in each unit is reversed. Therefore, the description is omitted. FIG. 22 shows a detailed time chart for the transmission operations of each unit in the case of FIG. 20B.

Figure 24:
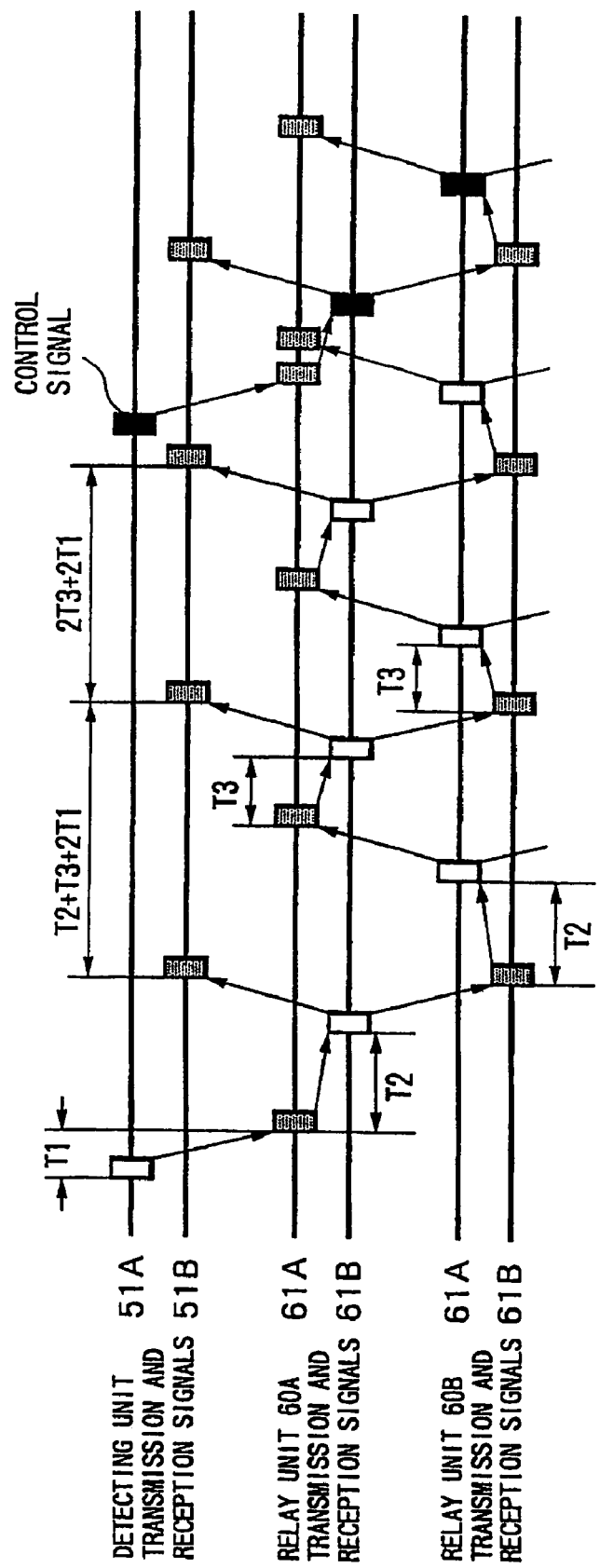
FIG. 24 is a time chart at a time of signal propagation operation in FIG. 23A.

Next is a description of the transmission operations in the case where there is a break in the vicinity of the relay unit 60C on the rail 11A between the relay unit 60B and the relay unit 60C, for example, with reference to FIG. 23 through FIG. 25.

FIG. 23A shows the transmission operations when a signal is transmitted from the ultrasonic transducer 51A in FIG. 20A, and FIG. 24 shows a detailed time chart for the transmitting and receiving operations of each unit in this case. FIG. 23B shows the transmission operations when a signal is transmitted from the ultrasonic transducer 51B in FIG. 20B, and FIG. 25 shows a detailed time chart of the transmitting and receiving operations of each unit in this case.

The transmission operations when a signal is transmitted from the ultrasonic transducer 51A as shown in FIG. 23A will be described.

Similarly to the case of FIG. 20A, a transmission signal from the ultrasonic transducer 51A of the detecting unit 50 is relayed in the order of solid line arrows A and B in FIG. 23A, to be received by the ultrasonic transducer 61B of the relay unit 60B, and a signal is transmitted from the ultrasonic transducer 61A of the relay unit 60B in bi-directions of the rail 11A as shown by a solid line arrow C. However, if there is a break, the signal of the arrow C transmitted from the ultrasonic transducer 61A of the relay unit 60B is not propagated to the relay unit 60C since it is reflected by the break. As a result, the relay unit 60C and the terminal unit 70 cannot receive ultrasonic waves, as shown in FIG. 24.

On the other hand, the signal of the arrow C, which has been propagated from the relay unit 60B in the left hand direction in FIG. 23, is received by the ultrasonic transducer 61A of the relay unit 60A similarly to the case where there is no break, transmitted from the ultrasonic transducer 61B of the relay unit 60A to the rail 11B again as shown by a solid line arrow D, to be received by the ultrasonic transducer 51B of the detecting unit 50 and the ultrasonic transducer 61B of the relay unit 60B again. In the case where there is no break, since the relay unit 60B receives a signal from the relay unit 60C after receiving the signal of the arrow D as shown in FIG. 21, it transmits a signal after the lapse of time T3 from when it receives the signal of the arrow D. However, in the case where there is a break, since there is no signal transmitted from the relay unit 60C, when time T3 has elapsed after receiving the signal of the arrow D as shown in FIG. 24, the relay unit 60B transmits a signal to the rail 11A as shown by a solid line arrow in FIG. 23A. As a result, in the case where there is a break, the second transmission timing of the relay unit 60B becomes earlier than the case where there is no break. The transmission signal of the arrow D is received by the relay unit 60A, and transmitted from the relay unit 60A to the rail 11B as shown by a solid line arrow F, to be received by the detecting unit 50. Accordingly, the reception timing of the reception signal based on the second transmission operation of the relay unit 60B in the detecting unit 50 is earlier than the case where there is no break, and thus the detecting unit 50 detects this earlier reception timing, to judge that there is a break.

When judging that there is a break, the detecting unit 50 transmits a control signal (shown by a black square in FIG. 24) to advise the relay units to stop relay operations. The control signal is transmitted to the relay units 60A and 60B in the order of broken line arrows G, H and I in FIG. 23A. On receiving the control signal, the relay units 60A and 60B stop relay operations after transmitting similar signals. Afterwards, the detecting unit 50 executes a transmission operation from the ultrasonic transducer 51B as shown in FIG. 23B in order to confirm whether or not the relay operation is normal so that ultrasonic waves can be propagated to the terminal unit 70.

Similarly to FIG. 20B, the transmission signal from the ultrasonic transducer 51B of the detecting unit 50 is relayed to the relay unit 60C via the relay unit 60A and the relay unit 60B in the order of solid line arrows A' through D' in FIG. 23B, and the signal is transmitted from the ultrasonic transducer 61A of the relay unit 60C in bi-directions of the rail 11A as shown by a solid line arrow D' in the drawing.

The signal of the solid line arrow D', which has been transmitted from the relay unit 60C and propagated in the right hand direction in the figure, is reflected by the break, and the reflected waves are received by the ultrasonic transducer 61A of the relay unit 60C. The relay unit 60C that has received the reflected waves, immediately transmits a reflected wave reception signal (shown by a symbol A in FIG. 25) indicating that reflected waves have been received, from the ultrasonic transducer 61B to the rail 11B as shown by a broken line arrow F' in the figure, and the relay unit 60B that has received this reflected wave reception signal, transmits a similar reflected wave reception signal A immediately from the ultrasonic transducer 61A to the other rail 11A as shown by a broken line arrow G', and the relay unit 60A that has received this, similarly transmits a reflected wave reception signal A immediately from the ultrasonic transducer 61B to the rail 11B as shown by a broken line arrow H', to be received by the detecting unit 50. The detecting unit 50 calculates the time (=T2−T3+2T1+Tr) from the reception of the previous signal to the reception of the reflected wave reception signal, and specifies the location of the break.

Here, the signal propagated from the relay unit 60C in the right hand direction in the figure is received by the terminal unit 70, a transmission signal from the terminal unit 70 is propagated to the detecting unit 50 in the order of the broken line arrows E' through H' similarly to the case where there is no break as shown in FIG. 22, and relay operations of the detecting unit 50 and each of the relay units 60A through 60C are stopped. Furthermore, by receiving the signal from the terminal unit 70, the detecting unit 50 judges that the operation of each unit is normal.

As described above, in a construction in which relay units are disposed between a detecting unit and a terminal unit, ultrasonic waves transmitted from the detecting unit are relayed to the terminal unit by the relay units using a failure detection target section as a transmission medium, and a signal from the terminal unit is transmitted to the detecting unit via the relay units in response, it is possible for only the detecting unit to be connected to a central processing unit by a communication line, and hence it is possible to simplify a failure detecting system network. Furthermore, in a construction in which ultrasonic transducers are installed such that ultrasonic waves are propagated in bi-directions, the ultrasonic wave transmitting and receiving faces of the ultrasonic transducers may be simply installed at right angles to the transmission medium. Therefore, installation environment restrictions are reduced, and hence the work of installing ultrasonic transducers is facilitated.

Moreover, for example, in a wireless communication network in which a large number of base stations are installed, since electrical power supplies and communication equipment for network connections are installed in the base stations, if detecting units are installed near the base stations, it is possible to utilize the existing network for another purpose, and also the interconnection length of the communication lines can be shortened. Accordingly, it is also possible to use the wireless train detecting system network as described above, it being ideal to use the failure detecting system in common with the wireless train detecting system.

Figure 1:
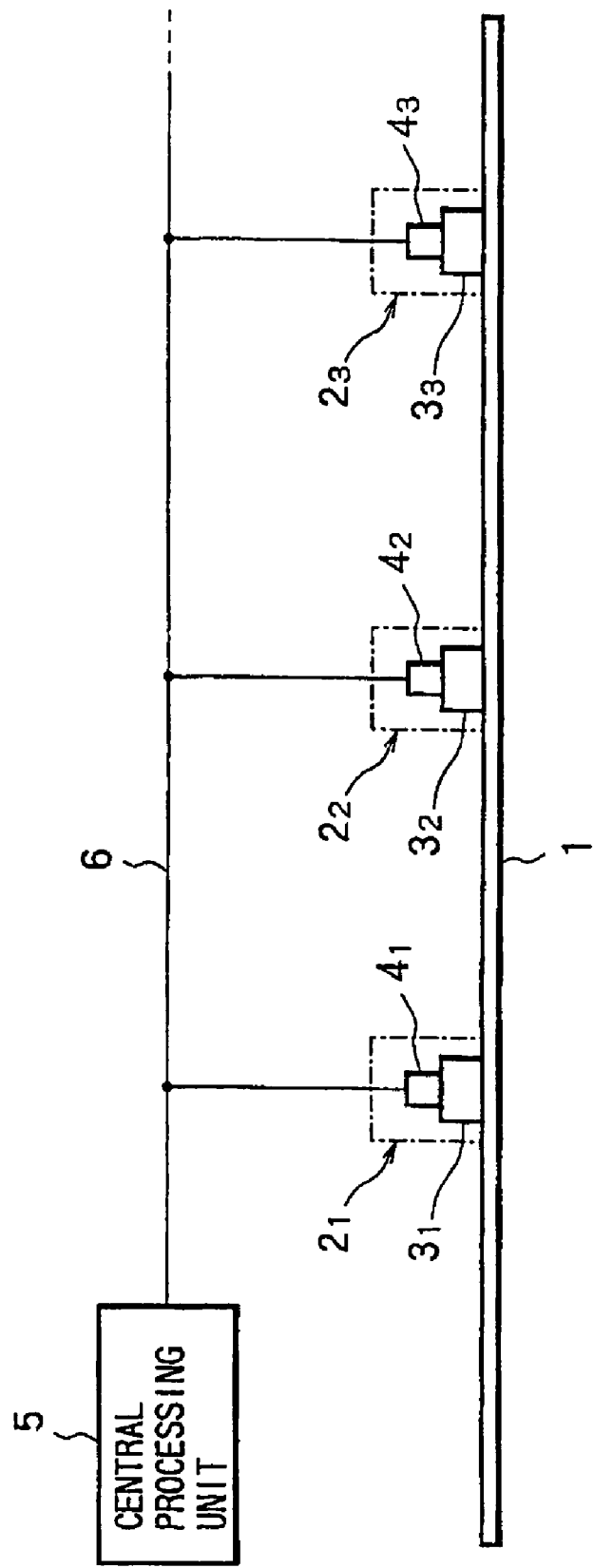
FIG. 1 is a block diagram showing an example of a conventional failure detecting system.

Furthermore, similarly to the conventional system in FIG. 1, in the case where the relay units and the terminal unit are also connected to the network in the construction in FIG. 2, failures can be monitored by both a failure detecting system using a network such as the conventional system, and a failure detecting system according to a construction of the present invention, in which the detection object is used as an information propagation medium. Such a system structure is a multiple redundancy system using physically different devices, and so safety is improved for failures occurring in either of the two systems.

The applications of the failure detecting system of the present invention are not limited to rails, and the system is applicable to pipes for fluid transfer, such as pipelines and the like, provided they are structures constructed over a long distance, through which ultrasonic waves can be propagated.

INDUSTRIAL APPLICABILITY

The present invention can simplify the structure of a failure detecting system for rails, pipelines and the like, which are constructed over a long distance. Therefore, its industrial applicability is high.

What is claimed is:

1. A failure detecting system, comprising a detecting unit, relay units and a terminal unit arranged along a detection object at intervals, and a sound wave is transmitted from the detecting unit and relayed by the relay units to the terminal unit using said detection object as a transmission medium, wherein said terminal unit receives the transmitted sound wave, the sound wave is returned from said terminal unit, and relayed by said relay units to said detecting unit, and said detecting unit judges whether or not there is a failure in said detection object based on the sound wave reception state in said detecting unit.

2. A failure detecting system according to claim 1, wherein said detecting unit judges whether or not there is a failure in said detection object, based on whether or not it has received the sound wave returned from said terminal unit.

3. A failure detecting system according to claim 2, wherein said detecting unit judges whether or not the sound wave returned from said terminal unit is received, based on whether or not said returned sound wave is received within a predetermined time range after the sound wave is transmitted.

4. A failure detecting system according to claim 1, wherein each of said relay units is provided with a first transmission and reception section that transmits and receives sound wave on the detecting unit side, and a second transmission and reception section that transmits and receives sound wave on the terminal unit side, and when said first transmission and reception section receives sound wave from the detecting unit side, said second transmission and reception section transmits sound wave to the terminal unit side, and when said second transmission and reception section receives sound wave from the terminal unit side, said first transmission and reception section transmits sound wave to the detecting unit side.

5. A failure detecting system according to claim 4, wherein upon receiving reflected sound wave from a failure of said detection object, said detecting unit specifies the location of said failure based on the time from when it transmits the sound wave to when it receives said reflected sound wave.

6. A failure detecting system according to claim 4, wherein upon receiving sound wave from said detecting unit side, said relay unit returns the sound wave from said first transmission and reception section to the detecting unit side.

7. A failure detecting system according to claim 6, wherein said detecting unit corrects the transmission speed of the sound wave, based on the time from when it transmits the sound wave to when it receives return sound wave from said first transmission and reception section of the adjacent relay unit.

8. A failure detecting system according to claim 4, wherein sound wave transmission levels of said relay unit and terminal unit are set to be almost the same as the sound wave reflection levels in the vicinity of where these units are arranged.

9. A failure detecting system according to claim 1, wherein said relay unit comprises at least a transmission and reception section that transmits and receives sound wave in the directions of both said detecting unit side and terminal unit side.

10. A failure detecting system according to claim 9, wherein said relay unit transmits a sound wave after the lapse of a preset time delay after receiving a sound wave, and said time delay is different between when sound wave is received for the first time and when sound wave is received at a second or later time.

11. A failure detecting system according to claim 9, wherein said terminal unit transmits a sound wave signal that is different from a sound wave signal transmitted from the detecting unit.

12. A failure detecting system according to claim 11, wherein when a received sound wave signal is a sound wave signal returned from said terminal unit, said relay unit transmits the same signal as the sound wave signal returned from the terminal unit.

13. A failure detecting system according to claim 12, wherein said relay unit stops the relay operation thereof after having transmitted the same signal as the sound wave signal returned from the terminal unit.

14. A failure detecting system according to claim 9, wherein when receiving reflected sound wave from a failure of said detection object, said relay unit relays a signal indicating reception of the reflected sound wave to advise the detecting unit.

15. A failure detecting system according to claim 14, wherein the signal indicating reception of said reflected sound wave is different from any of a sound wave signal transmitted from the detecting unit and a sound wave signal returned from the terminal unit.

16. A failure detecting system according to claim 9, wherein the transmission and reception sections of each of said detecting unit, relay unit and terminal unit are installed on at least a pair of detection objects that are separated acoustically from each other, a sound wave signal transmitted from said detecting unit is transmitted to each of said pair of detection objects alternately to be relayed to the terminal unit via said relay unit, a sound wave returned from the terminal unit is transmitted to each of the pair of detection objects alternately to be sent to the detecting unit via the relay unit, and also a sound wave signal is transmitted from the detecting unit to each of said pair of detection objects alternately.

17. A failure detecting system according to claim 16, wherein upon judging that the sound wave propagation state is abnormal, based on the sound wave reception state, said detecting unit transmits a control signal to advise the relay units and the terminal unit to stop relay operations.

18. A failure detecting system according to claim 17, wherein after having transmitted said control signal, said detecting unit transmits a signal to confirm that the relay operations of the relay unit and the terminal unit are normal.

19. A failure detecting system according to claim 1, wherein said detection object is a rail.

\* \* \* \* \*